United States Patent
Denisov et al.

(10) Patent No.: US 6,681,186 B1
(45) Date of Patent: Jan. 20, 2004

(54) SYSTEM AND METHOD FOR IMPROVING THE ACCURACY OF DNA SEQUENCING AND ERROR PROBABILITY ESTIMATION THROUGH APPLICATION OF A MATHEMATICAL MODEL TO THE ANALYSIS OF ELECTROPHEROGRAMS

(75) Inventors: Gennady A. Denisov, Arcadia, CA (US); Alan B. Arehart, Passdena, CA (US); Michael D. Curtin, El Segundo, CA (US)

(73) Assignee: Paracel, Inc., Pasadena, CA (US)

( * ) Notice: Subject to any disclaimer, the term of this patent is extended or adjusted under 35 U.S.C. 154(b) by 0 days.

(21) Appl. No.: 09/658,161

(22) Filed: Sep. 8, 2000

(51) Int. Cl.[7] .......................... G06F 19/00; C12Q 1/68; G11C 17/00
(52) U.S. Cl. ................. 702/20; 435/6; 365/94
(58) Field of Search .................. 702/19, 20; 435/6; 365/94

(56) References Cited

U.S. PATENT DOCUMENTS

| | | | |
|---|---|---|---|
| 5,453,247 A | 9/1995 | Beavis et al. | |
| 5,502,773 A | 3/1996 | Tibbetts et al. | |
| 5,618,672 A | 4/1997 | Stodola et al. | |
| 5,733,729 A | 3/1998 | Lipshutz et al. | |
| 5,853,979 A | 12/1998 | Green et al. | |
| 5,871,697 A | 2/1999 | Rothberg et al. | |
| 5,873,052 A | 2/1999 | Sharaf | |
| 5,964,860 A | 10/1999 | Peterson et al. | |
| 5,966,711 A | 10/1999 | Adams | |
| 5,970,500 A | 10/1999 | Sabatini et al. | |
| 6,015,667 A | 1/2000 | Sharaf | |
| 6,025,136 A | 2/2000 | Drmanac | |
| 6,047,109 A | 4/2000 | Whittaker | |
| 6,054,270 A | 4/2000 | Southern | |
| 6,195,449 B1 | * 2/2001 | Bogden et al. | |
| 6,236,944 B1 | * 5/2001 | Miller et al. | |

OTHER PUBLICATIONS

Ewing, Brent et al., "Base–Calling of Automated Sequencer Traces Using Phred. I. Accuracy Assessment", *Genome Research*, pp. 8:175–185, 1998.

Ewing, Brent and Green, Phil, "Base–Calling of Automated Sequencer Traces Using Phred. II. Error Possibilities", *Genome Research*, pp. 8:186–194, 1998.

* cited by examiner

Primary Examiner—John S. Brusca
(74) Attorney, Agent, or Firm—Hugh J. Pasika

(57) ABSTRACT

A system and method for improving the accuracy of DNA sequencing and error probability estimation through application of a mathematical model to the analysis of electropherograms. The method includes processing a plurality of information obtained from a base calling system and creating a plurality of refined base calls using a plurality of original base calls and a plurality of intrinsic peak characteristics. A quality value is also assigned to each of the plurality of refined base calls using the plurality of intrinsic peak characteristics. Processing comprises detecting a plurality of peaks, expanding the plurality of peaks, and resolving the plurality of expanded peaks. Resolving may include fitting the plurality of expanded peaks using a model of a peak shape. A peak resolution parameter is calculated and used in processing. The system may also be trained.

54 Claims, 12 Drawing Sheets

SYSTEM AND METHOD FOR IMPROVING THE ACCURACY OF DNA SEQUENCING AND ERROR PROBABILITY ESTIMATION THROUGH APPLICATION OF A MATHEMATICAL MODEL TO THE ANALYSIS OF ELECTROPHEROGRAMS

BACKGROUND

A. Field of the Invention

This invention relates to deoxyribonucleic acid (DNA) sequencing. More specifically, this invention provides a method and system for improving the accuracy of DNA sequencing and error probability estimation through application of a mathematical model to the analysis of electropherograms.

B. General Description of the Area of Research

With the advent of the Human Genome Project and its massive undertaking to sequence the entire human genome, researchers have been turning to automated DNA sequencers to process vast amounts of DNA sequence information. DNA, or deoxyribonucleic acid, is one of the most important information-carrying molecules in cells. DNA is composed of four different types of monomers, called nucleotides, which are in turn composed of bases linked with a sugar and a phosphate group. The four bases are adenine (A), cytosine (C), guanine (G), and thymine (T). The original state of a DNA fragment is a double helix of two antiparallel chains with complementary nucleotide sequences. The coded information of a DNA sequence is determined by the order of the four bases in either of these chains.

A common approach to obtaining information from DNA is the Sanger method. In this method, single-stranded DNA fragments are used as templates from which a series of nested subfragment sets is generated. (F.Sanger, et al., "DNA Sequencing With Chain-Terminating Inhibitors", *Proceedings of the National Academy of Sciences of the USA*, vol. 74, pp.5463–5467 (1977)). The subfragments start at the same end of the template, and a fraction of the subfragments of each length are caused to terminate by incorporation of chemically modified bases, thereby forming subfragment sets in increments of one nucleotide. In the popular "four-color" method, the terminating bases are labeled by one of four fluorescent dyes specific to the terminating base type, A, C, G or T. (L. M. Smith, et al., "Fluorescence Detection In Automated DNA Sequence Analysis", *Nature*, vol. 321, pp. 674–679 (1986)). The resulting mixture of sets of subfragments represents all of the possible sublengths of the template, with each set of subfragments labeled by a fluorescent dye corresponding to its terminating base type. To determine the sequence of the template, the subfragments are sorted by length using electrophoresis. In this process shorter subfragments migrate faster than longer subfragments in an applied electric field. Because subfragments are created in increments of one nucleotide, they pass through an electrophoretic cell one at a time in the order of the nucleotides in the template. The terminating base types are identified by the wavelength at which they fluoresce. A real-time fluorescent detection of migrating bands of the subfragments is then performed as the subfragments pass through a detection zone. The light collected is processed with a set of spectral filters that attempt to isolate the signals from the four dyes.

In automated DNA sequencing, these raw signals are then analyzed by a signal processing software. The steps of signal processing may include downsampling of the data to 1 Hz if necessary, primer data removal, baseline adjustment, noise filtering, multicomponent transformation, dye mobility shift correction, signal normalization, etc. (see, e.g., M. C. Giddings, et al., "A Software System For Data Analysis In Automated DNA Sequencing", *Genome Research*, vol. 8, pp. 644–665 (1998)). Processing the raw data produces analyzed electropherograms with clearly defined peaks. The analyzed data in the form of electropherograms are then processed using a base calling program. The base calling program infers a sequence of bases in the DNA fragment. This sequence of bases is also referred to as a read and is usually about 1,000 bases long. Not all of the called bases are used in subsequent processing. The statistically averaged error produced by any base calling program is usually low, i.e., below 1%, for bases located near middle of a read and increases significantly toward the beginning and, especially, toward the end of a read. To characterize a reliable, or high quality part of a read, a threshold of 1% base calling error is commonly accepted. That is, only that part of the read having an average base calling error of 1% or less will be subsequently used. Alternatively, this may be characterized in terms of the quality values assigned to bases, where the quality is the measure of reliability of the base call. According to a commonly used definition of quality values, a quality value of 20 or higher corresponds to a probability of error of 1% or less. In practice, when sequencing, the correct sequence is not known in advance, so reliable predictions of quality values for newly sequenced fragments based on previous training or calibration on a data set with a known correct sequence are desirable.

C. Prior Art

1. ABI Base Caller

The ABI Base Caller is a part of DNA Sequencing Analysis software produced by Applied Biosystems of Foster City, Calif. This program takes raw electropherograms as input, processes them to produce analyzed electropherograms having well defined and evenly spaced peaks, and then detects and classifies peaks in the analyzed electropherograms as a sequence of bases. The program outputs the results to a binary file called an ABI sample file. The output includes the raw and analyzed electropherograms for each of the four traces, the array of called bases and the array of locations assigned to the bases in an electropherogram. The output does not include an estimate of quality values, because the ABI Base Caller program does not estimate the reliability of base calls.

The ABI Base Caller was chronologically the first and is still one of the best base calling programs available. The base calls produced by the ABI Base Caller, however, are not very accurate toward the end of a read, where peaks in an analyzed electropherogram become wider and significantly overlap. In this part of the read, the ABI Base Caller produces a considerable amount of mismatch errors, unknown base calls that are denoted as N's, and overlooks some base calls resulting in deletion errors.

2. Phred

Phred is the first base calling software program to achieve a lower error rate than the ABI software, and is especially effective at the end of a read. Phred takes analyzed electropherograms produced by the ABI Base Caller as input, calls the bases and assigns quality values to the called bases. (see B. Ewing, et al., "Base Calling Of Automated Sequencer Traces Using Phred. I. Accuracy Assessment", *Genome Research*, vol. 8(3), pp. 175–185 (1998); B. Ewing and P. Green, "Base-Calling Of Automated Sequencer Traces Using Phred. II. Error Probabilities", *Genome Research*, vol. 8(3), pp. 186–194 (1998)).

The base calling procedure in Phred consists of four phases: locating the predicted peaks, locating the observed peaks, matching the observed and predicted peaks, and finding the missed peaks. In the first phase, Phred attempts to find the idealized locations that all of the base peaks that would have occurred in the absence of imperfections in the sequencing reactions, in the electrophoresis process, and in trace processing. The underlying premise of Phred is that under such idealized conditions, each trace consists of evenly spaced, non-overlapping peaks, corresponding to the labeled fragments that terminate at a particular base in the sequenced strand. To find the positions of predicted peaks, Phred first examines the four trace arrays that correspond to each of the four bases to detect the peaks. A detected predicted peak is identified as the location of the maximum value, or, if the maximum does not exist, the midpoint between the inflection points. The processed trace is then scanned to find the regions of uniform peak spacing and the average peak period. The average peak period corresponds to peak-to-peak spacing or inter-peak spacing. This is determined for each of the regions. Phred then uses Fourier methods to find the positions of the predicted peaks in between these regions.

In the second phase, Phred locates all of the observed peaks by scanning the four trace arrays for regions that are concave. According to Phred, the concave part of the trace located between two inflection points is the observed peak. In the third phase, Phred matches observed and predicted peaks by assigning each observed peak to each predicted peak. This is done via alignment of the two lists of peaks using a dynamic programming algorithm. If, upon the completion of the third phase, no suitable observed peak can be assigned to a predicted peak, the corresponding base call is defined to be N, meaning that it is unknown or that it is not assigned.

Once the base calling procedure is completed, Phred assigns quality values to the bases. The quality value is the measure of reliability of a given base call. If P is the probability that the base call is incorrect, then the quality value QV is defined by the expression $QV = -10 \log P$, rounded to the nearest integer. Thus, $P=10^{-1}$ corresponds to QV=10;

$P=10^{-2}$ corresponds to QV=20;

$P=10^{-3}$ corresponds to QV=30.

etc.

To assign quality values to called bases, Phred trains on established data for which the correct base sequence, referred to as a consensus, is already known. Phred's training software compares the actual base calls with the consensus to determine the positions at which Phred makes base calling errors. Phred then stores the trace conditions under which a particular peak was incorrectly called. Specifically, for each called base or peak, Phred computes and stores four parameters, peak height ratio in a window of three peaks, peak height ratio in a window of seven peaks, peak spacing ratio in a window of seven peaks and peak resolution. These four parameters are referred to as the trace parameters. These parameters are useful in discriminating base calling errors from correct base calls. For each base, these four parameters are expressed as functions of characteristics of the corresponding peak, as well as the characteristics of several other peaks flanking the current peak. Smaller trace parameter values correspond to higher quality measurements.

Based on this stored information, a text file called a lookup table is generated by Phred's training software. This file stores information about average base calling errors that corresponds to each given set of the four trace parameter values. The lookup table is provided to users of Phred as a part of the source code and is used when assigning quality values to called bases. Phred's lookup table is calibrated on data generated by the ABI PRISM® 377 DNA Sequencer (available from Applied Biosystems of Foster City, Calif.). When Phred is run on data produced by the newer generation DNA sequencers (e.g., ABI PRISM® 3700 DNA Analyzer), the quality values produced are not very accurate. Specifically, the quality values determined by Phred are lower than those experimentally produced, causing false low quality determinations that result in unused base calls.

D. Inadequacies of the Prior Art

Currently used tools for automated DNA sequencing such as ABI's Base Caller, Phred and others operate with peak characteristics, such as area, position, height, etc. (see, e.g., A. Berno, "A Graph Theoretic Approach To The Analysis Of DNA Sequencing Data", *Genome Research*, vol. 6, pp.80–91 (1996); M. C. Giddings, et al., "A Software System For Data Analysis In Automated DNA Sequencing", *Genome Research*, vol. 8, pp. 644–665 (1998)). These characteristics are used to discern true peaks from noise before performing base calling, as well as to compute important trace parameters, which are used to calibrate quality values assigned to called bases. To compute the characteristics of a peak of a given dye color, the signal from the trace of the particular color is used. Because this signal is actually a sum of individual signals from all peaks of the particular color, the presence or absence of other peaks of the same color in close vicinity of a given peak significantly affects the characteristics computed for a given peak. For example, the apparent height of a given peak computed as the total signal at the peak's position would generally overestimate the true, or intrinsic height of this peak. This occurs because other peaks of the same color which overlap with the current peak amplify the signal at the current peak's position. These characteristics, therefore, are not very accurate and should be considered as "apparent". The phenomenon of peak overlapping is particularly noticeable toward the end of a trace, which corresponds to the end of a fragment. Toward the end of a trace, peaks become wider and overlap, so that the difference between the apparent and intrinsic peak characteristics becomes significant. And it is toward the end of a trace where the currently used, prior art base calling systems fail to provide accurate results.

FIG. 1 (prior art) illustrates a sample electropherogram showing inflection points, apparent peaks and apparent peak positions as identified by Phred. Phred uses inflection points to detect peaks which are more accurately described as apparent peaks. A peak is defined as the concave part of an electropherogram, E, located between two inflection points. Inflection points $i_1$ through $i_8$ are used to identify peaks $P_1$, $P_2$, $P_3$ and $P_4$. Only the shaded areas in FIG. 1 are regarded as the peak area and are used in subsequent processing. The rest of the electropherogram, where the signal may still be high, is ignored by Phred, therefore ignoring this useful information. This may be a considerable loss if two or more peaks overlap, such as with peaks $P_2$, $P_3$ and $P_4$.

The apparent peak characteristics are computed in Phred in the following way. Apparent peak area is the area below the apparent peak. Apparent peak position is the position in an electropherogram which bisects the apparent peak's area and is shown as $POS_1$, $POS_2$, $POS_3$ and $POS_4$. Apparent peak height is the signal at the apparent peak position. Apparent peak spacing is the distance between the positions of one apparent peak and a previous apparent peak in an electropherogram.

Partially due to inadequate processing of traces and peaks, toward the end of a trace, the commonly used base calling programs, such as Phred and the ABI Base Caller, produce a considerable number of unknown base calls designated as N. This happens, for example, when two or more good peak candidates for base calling are found at a given position in the trace or, conversely, when no peaks are found near the position where a base call should be made. Because Ns are not present in the correct sequence, they may be regarded as mismatch errors. From a practical point of view, it is desirable to re-call Ns to a best guess base call and express the uncertainty associated with the base through an assigned quality value.

Another form of inadequate trace processing results in missed bases, or deletion errors, produced, particularly, by the ABI Base Caller towards the end of read. This may occur when two or more overlapped peaks are mistakenly identified and called as one. To avoid this type of error, Phred splits excessively wide peaks into narrower peaks. However, Phred's peak splitting procedure may be inaccurate and may result in undesired consequences which include the splitting and subsequent calling of noise peaks, such as dye blobs, the peaks corresponding to a pure dye, rather than to any DNA subfragment.

Inadequate processing of peaks not only affects base calling, but may also result in assigning inaccurate quality values to bases. The apparent peak characteristics and apparent trace parameters that are used by prior art systems such as Phred to assign a quality value to a called peak depend significantly on the peak's environment. That is, whether there are other peaks of the same dye color in a close vicinity of the current peak. Because the environment of an average peak may vary significantly from one dataset to another, quality values assigned to bases of one dataset based on a quality value calibration derived from another dataset may produce inaccurate results. Specifically, Phred, which is calibrated using the data produced by ABI PRISM® 377 DNA Sequencers, may underestimate quality values of bases generated by the ABI PRISM® 3700 DNA Analyzer.

Even if proper calibration is used, Phred usually assigns low quality values to unresolved bases. Unresolved bases are typically present near the end of a read. A base is unresolved if it is called as N or if for at least one of its neighboring bases, there is no point between two corresponding peaks at which the signal is less than the signal at each peak. Thus, with an improved base calling and peak processing procedure that includes the re-calling of Ns and resolving of unresolved bases, higher and more accurate quality values may be assigned to bases. This improved processing may also produce more useful data by increasing the number of bases with sufficiently high quality values, such as 20 or better.

BRIEF SUMMARY OF THE INVENTION

The present invention provides a novel approach to peak processing using intrinsic peak characteristics in computations related to base calling and quality value calibration instead of the apparent characteristics that are used in prior art systems. The use of intrinsic characteristics allows for more accurate base calls and quality value assignments. The method of the present invention is based on the application of a mathematical model of peak electrophoresis to discern true peaks from noise and to process rows of overlapping peaks of a given color. The processing of the present invention includes three steps: peak detection, peak expansion and peak resolution. The first step employs inflection points to find individual peaks. The peak boundaries are then expanded by scanning the trace to the left from the left boundary of each peak and scanning the trace to the right from the right boundary of each peak. Finally, the groups of overlapping peaks are resolved into individual intrinsic peaks. For single peaks, the resolution step consists of simply fitting the data peak with the model. For multiple peaks, resolution requires a more sophisticated iterative procedure.

The mathematical model of peak electrophoresis is further used to discern true peaks from noise. The expected shape of a current peak is computed as an average shape of a group of previous good peaks that were refined according to the model. By comparing an expected shape of a current peak with the shape of a current peak, a determination is made whether the current peak is a true peak or is noise so that only true peaks are called.

The present invention also resolves wide peaks into descendent peaks more accurately than prior art systems. If the width of a current peak is greater than a system specified expected width, the peak will be resolved into two or more intrinsic peaks having model peak characteristics. Certain adjustable parameters of these descendent peaks are selected so as to fit the observed data. In this way, the sum of the signals of the multiple superimposed intrinsic peaks are approximately equal to the apparent signal of the original parent peak.

The present invention increases the usefulness of DNA data by calling bases which are unassigned and unassignable by prior art systems. By re-calling originally unknown bases, inserting new bases and resolving overlapping peaks, the useful read length of bases with high quality values is extended.

DETAILED DESCRIPTION

A. Overview of the Invention

Figure 1:
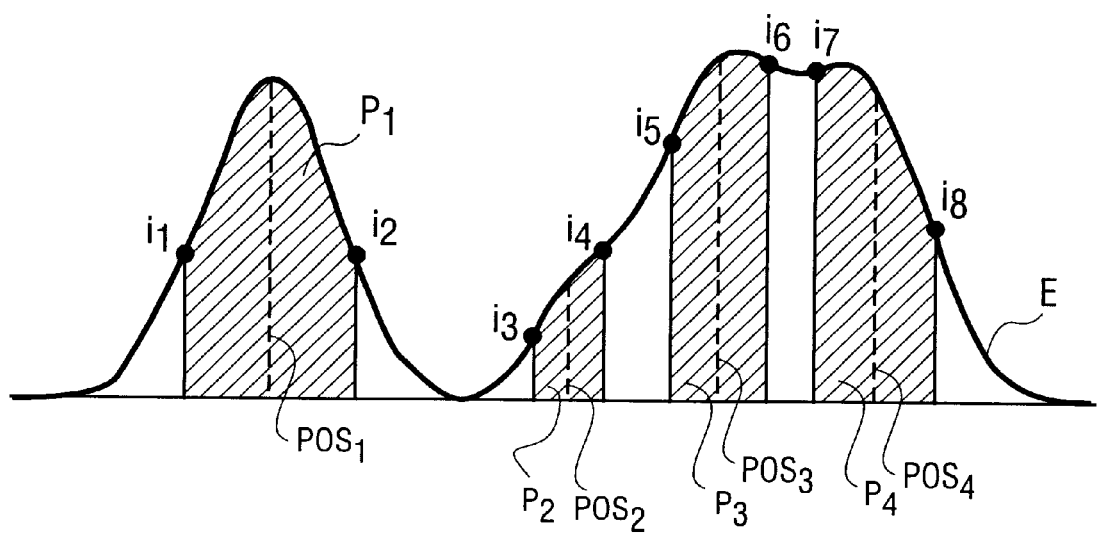
FIG. 1 (prior art) depicts a sample electropherogram showing inflection points, apparent peaks, and apparent peak position as identified by Phred

The present invention provides a novel approach to peak processing. This approach uses the intrinsic peak characteristics in computations related to base calling and quality value calibration instead of the apparent characteristics that are used in prior art systems. The use of intrinsic characteristics allows for more accurate base calls and quality value assignments.

Another aspect of the present invention is a method for computing intrinsic peak characteristics. The method of the present invention is based on application of a mathematical model of a peak electrophoresis, which results in an expression for the peak shape, to processing of rows of overlapping peaks of a given color. The processing of the present invention includes three steps: peak detection, peak expansion and peak resolution. The first step employs inflection points to find individual peaks. The peak boundaries are then expanded by scanning the trace to the left from the left boundary of each peak and scanning the trace to the right from the right boundary of each peak. The purpose of peak expansion is to include the entire electropherogram with nonzero intensity of signal and to find all groups or rows of overlapping peaks in each trace. The number of peaks in the group may vary from one, for a single peak, to more than ten, which is characteristic of the signal toward the end of trace, where peaks are wide and may overlap. Finally, the groups of overlapping peaks are resolved into individual intrinsic peaks superimposed over the overlapping peaks. For single peaks, the resolution step consists of simply fitting the data peak with the model. For multiple peaks with more than one peak in the group, resolution requires a more sophisticated iterative procedure which is discussed in more detail below.

Yet another aspect of the present invention is the use of the mathematical model of a peak electrophoresis to discern true peaks from noise. The present invention includes a simple model that takes into account the two basic physical processes involved in electrophoresis: the electromigration of DNA fragments in an applied electric field and their Brownian diffusion. Electromigration is responsible for the translation of a peak without changing its shape, while diffusion results in evolution of the peak shape. This model assumes that, initially, each peak has a rectangular shape with a finite width and predicts that the peak shape at any time is a function of three adjustable parameters. Two of these parameters are locally invariant. That is, these two parameters have nearly identical values for peaks that are close neighbors in the trace. Thus, the expected values of these parameters, and hence the expected shape of a current peak, can be determined by scanning the trace toward the beginning of the trace from a current peak and finding and fitting a few closely distanced good peaks. By comparing the expected shape of the current peak, computed as an average shape of a few previous good peaks, with the actual current peak's shape, the present invention determines whether the current peak is a true peak or noise. This determination is used when calling peaks.

Phred also uses average characteristics of a few previous peaks to determine or correct some characteristics of a current peak. More specifically, Phred compares the width of a current peak, defined as the distance between a couple of inflection points, with the average width of a few previous peaks. If the current peak is found to be wider than a system-specified width, the peak is split into two or more narrower peaks by bisecting, trisecting, etc. the peak. However, as discussed above, the peak width, as defined in Phred, is an apparent characteristic, which does not correspond to a physical, real characteristic of a peak. This is particularly important when peaks overlap. As such, the peak splitting procedure implemented in Phred is relatively crude and inaccurate. In particular, Phred is not capable of recognizing dye peaks, which correspond to pure dye rather than to DNA subfragment. Dye peaks have a characteristic shape and should not be called. Phred may processes dye peaks as regular wide peaks, by splitting them and subsequently calling the descendent peaks. The peak processing system of the present invention, bases a determination of the shape of a current peak on a comparison with the shape expected from the model and resolves complex peaks into individual peaks in a more natural way. According to the method of the present invention, if the current peak's width is found to be greater than a system specified expected width, the peak will be resolved with two or more intrinsic peaks that, by definition, have model peak characteristics. The adjustable parameters of these descendent peaks, including their heights, widths and positions, are selected so as to fit the observed data. In this way, the sum of the signals of the superimposed intrinsic peaks are approximately equal to the apparent signal of the original, current peak.

The method of the present invention increases the usefulness of DNA data. Bases which are unassigned and unassignable by prior art systems are called. In particular, when refining Ns produced by either the ABI Base Caller or by Phred, the traces in which the original locations of N calls fall into uncalled peaks are considered, and, among such traces, those with the highest intrinsic peaks are selected. The present invention also increases the usefulness of DNA data by inserting bases missed during an original base call analysis. As discussed above, the ABI Base Caller typically produces deletion errors toward the end of a read. As an improvement, the method of the present invention includes scanning the list of all peaks to find good peaks that were not called by the ABI Base Caller and inserting corresponding bases into the called sequence. When selecting appropriate candidate peaks, the present invention uses intrinsic peak characteristics. More specifically, an uncalled peak is considered a candidate for insertion if it is not truncated and its intrinsic height is greater than the intrinsic signal of any other peak at the candidate peak's position.

Further, the method of the present invention modifies the definitions for three trace parameters used in prior art systems, such as Phred, to calibrate quality values. To compute these parameters, the present invention uses intrinsic peak heights and positions instead of apparent values used by prior art systems such as Phred. The method of the present invention also introduces a new trace parameter, peak resolution, which is entirely different from a parameter of the same name used by Phred.

Because of the way Phred defines its fourth parameter, Phred typically assigns low quality values to unresolved bases and the bases close to unresolved bases in the read, which may result in false error values. A base is unresolved or unknown if it is called as N or if for at least one of its neighboring bases, there is no point between two corresponding peaks at which the signal is less than the signal at each peak. The method of the current invention, however, does not leave unresolved bases. The method of the current invention, re-calls Ns and resolves overlapping peaks. This significantly extends the useful read length estimated as a number of bases with sufficiently high quality values, such as 20 or better, in a read.

B. A Hardware Environment

Figure 2:
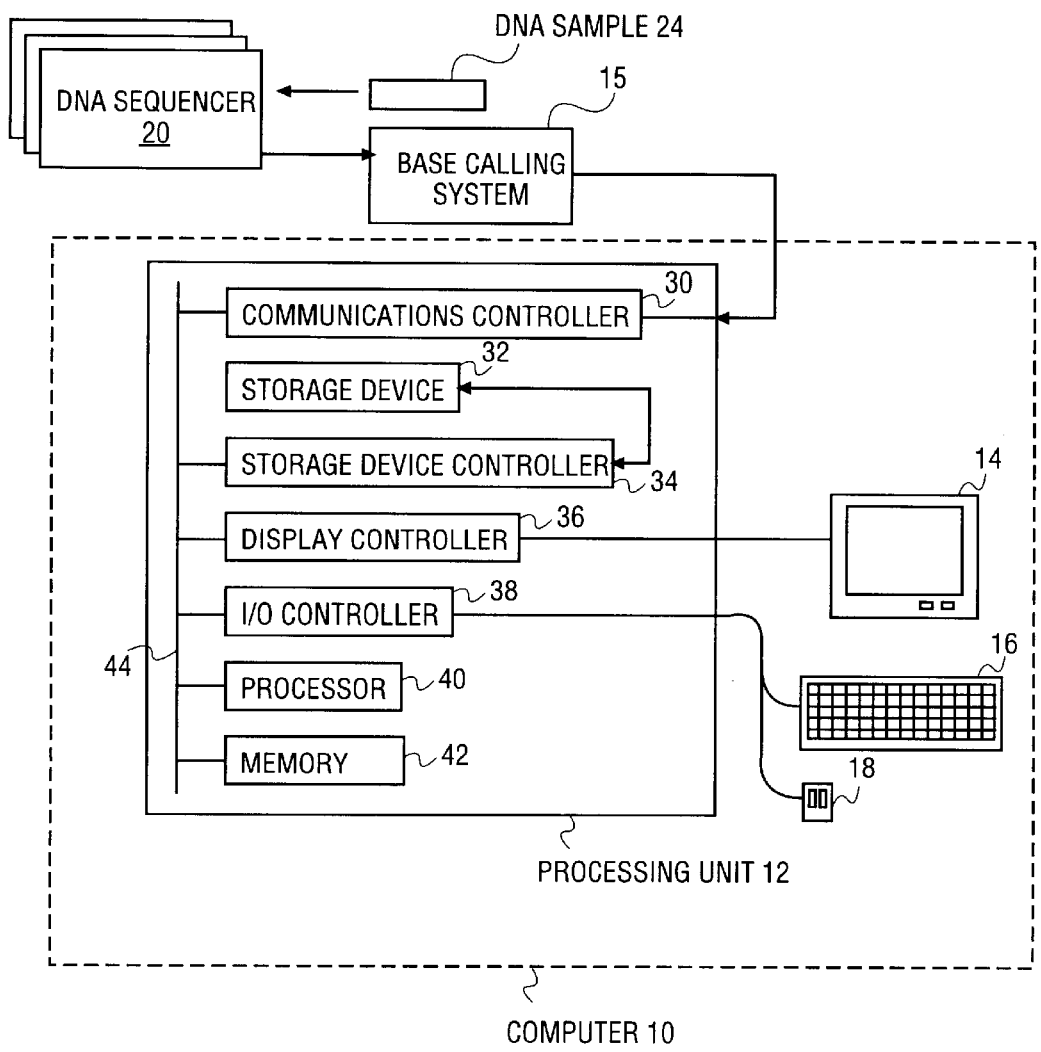
FIG. 2 depicts a hardware environment in which the method and system of the present invention may be implemented.

FIG. 2 depicts a hardware environment in which an embodiment of the method and system of the present invention may be implemented. In this embodiment, the method is implemented as software stored in and executed by a computer such as computer 10. Computer 10 may be any computer that can execute the software programs that receive data from base calling system 15 that includes DNA analyzing software which is executing on a computer. Base calling system 15 receives electropherogram data, also known as raw data, from a DNA sequencer, such as DNA sequencer 20. DNA sequencer may be any DNA sequencer or analyzer such as, for example, the ABI PRISM® 377 DNA Sequencer or ABI PRISM® 3700 Analyzer available from Applied Biosystems of Foster City, Calif. Base calling system 15 may be any base calling system, such as, for example, ABI PRISM® Sequencing Analysis Software version 3.4 available from Applied Biosystems of Foster City, Calif., which includes the ABI Base Caller as one of its components, and is referred to herein as the ABI Base Caller. In one embodiment, one or more DNA sequencers 20 may provide raw data to one base calling system 15. DNA sequencers 20 receive DNA samples 24, processes the DNA sample, and send information in the form of electropherogram data, also referred herein to as a DNA sample file, to base calling system 15. Base calling system 15 sends information to and may receive information from computer 10 via communications controller 30. Communications controller 30 and base calling system 15 must share a well known communications protocol, such as, for example, serial, parallel, and any variations thereof. In another embodiment, a plurality of DNA sequencers may be connected to a base calling system over a computer network. In this embodiment, computer 10 may communicate with base calling system 15 via a computer network (not shown).

In one embodiment, computer 10 comprises processing unit 12, display device 14, and one or more input devices, such as keyboard 16 and mouse 18. In this embodiment, processing unit comprises processor 40 and memory 42. Processor 42 may be any computer processor, and memory 40 may be any random access memory (RAM) or other readable and writeable memory device. Processor 40 executes the software that implements the method of the present invention utilizing memory 42. Information, including software that implements the method of the present invention, DNA sample files, etc. are read from and written to storage device 32 which is coupled to storage device controller 34. Storage device 32 may be a hard disk drive, a readable and writeable compact disk (CDRW) drive, a floppy disk drive, etc. Storage device 32 may be any device by which a machine may read from a machine readable medium such as the devices already mentioned, as well as, but not limited to, a stick or card memory device, a digital audio tape (DAT) reader, etc. In one embodiment, storage device 32 may be a plurality of disk drives comprising a disk array or other configuration. The processor may communicate instructions to display controller 36 to display images on display device 14. Display controller 36 may be any display controller, and display device 14 may be any display monitor, including, but not limited to, a cathode ray tube (CRT) display monitor and a thin film transistor (TFT) display screen. A system user may access computer 10 via any computer input device, such as, for example, keyboard 16 and mouse 18 which are coupled to the processor by I/O controller 38.

Processor 40, memory 42, storage device controller 34, display controller 36, I/O controller 38, and communications controller 30, are coupled to one another via and communicate with one another over bus 44. Bus 44 may be any bus that provides for communication of and between components within a computer. Although only one bus is depicted, multiple buses may be used in computer 10. In addition, other components and controllers (not depicted) or multiple instances of depicted components and controllers may be included in computer 10.

The present invention reads input data from DNA sample files stored on the storage device in either ABI format or SCF format. Each DNA sample file contains information about one DNA fragment and is approximately 1000 bases long. More specifically, the present invention reads a plurality of information from DNA sample files. First, the total number of called bases in the DNA fragment and the sequence of these bases is read. This sequence is referred to as original base calls and may be determined by any third party's base calling system, such as, for example, the ABI Base Caller. Second, the locations of the original base calls in the electropherogram, which may be referred to as called locations, are read. Last, the number of data points in each of four electropherograms and four analyzed electropherograms, which are represented in the form of integer arrays, are also read.

The present invention improves the base calls and locations read from the sample file and assigns a quality value to each base call. The results are then output in one or more output files in one or more of a variety of common formats compatible with prior art systems. A file in a first output format, the Phred compatible .phd file, consists of a header followed by three columns of data that contain the base calls, assigned quality values, and base locations. A file in a second output format, the qual file, consists of a header followed by the quality values assigned to the called bases, separated by spaces. A file in a third output format, the .seq file, consists of a header followed by a sequence of called bases. A file in a fourth output format, the .qr file, consists of data used to plot histograms of read length distribution for a given set of fragments. The data in the fourth output file format are comprised of two columns of information. The first column represents a bucket of read lengths, and the second column includes the number of fragments read having a quality value of 20 or more for a given bucket.

C. A Method

Figure 3:
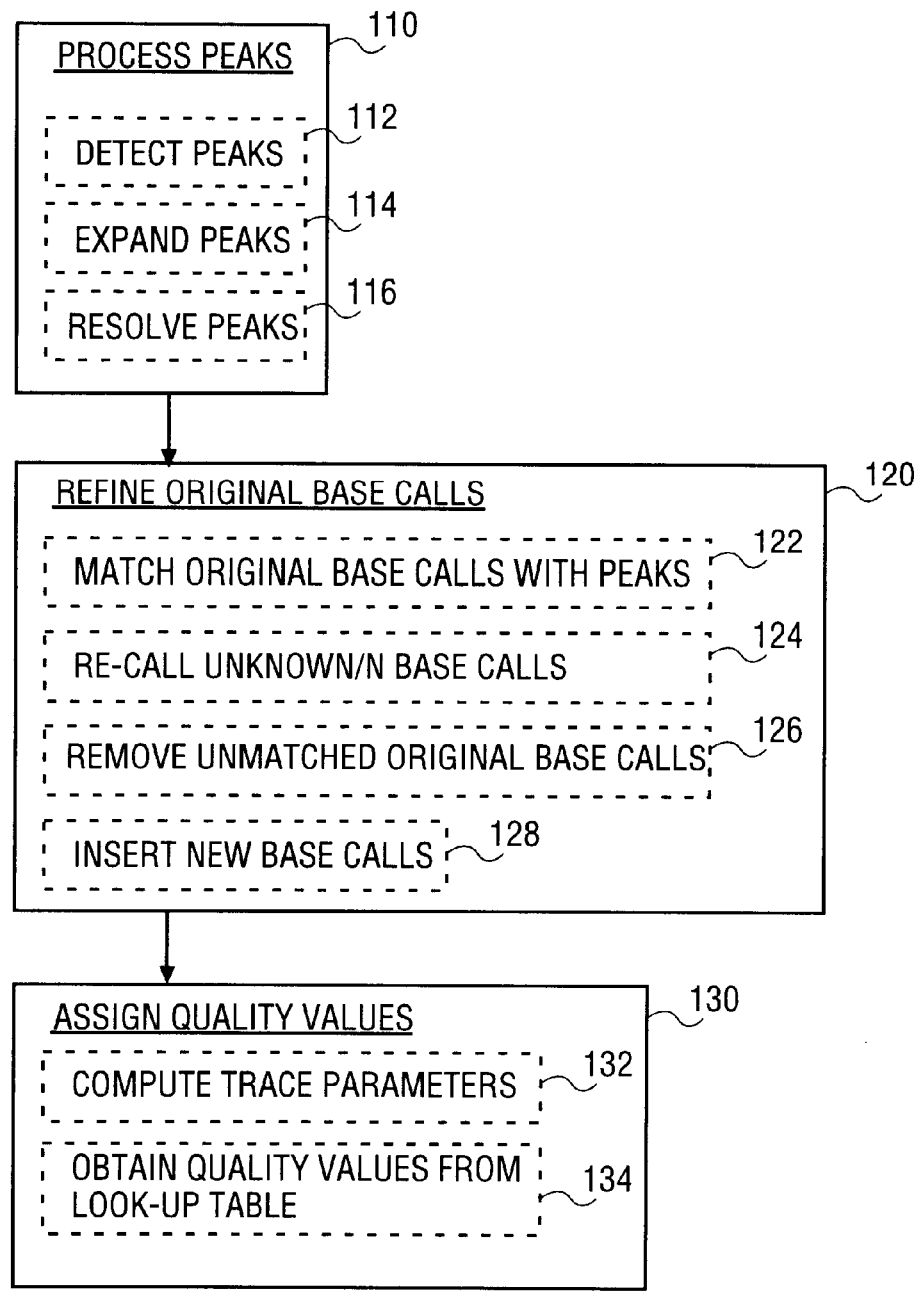
FIG. 3 depicts a general flow of actions taken according to one embodiment of the method and system of the present invention.

FIG. 3 depicts a general flow of actions taken according to one embodiment of the method and system of the present invention. The present invention comprises three basic steps: peak processing, as shown in block 110, refining base calls, as shown in block 120, and quality value assignment, as shown in block 130. In one embodiment, peak processing may include detecting peaks, as shown in block 112, expanding peaks, as shown in block 114, and resolving multiple peaks, as shown in block 116. In one embodiment, refining base calls may include matching original base calls with peaks, as shown in block 122; re-calling unknown bases, as shown in block 124; removing unmatched original bases, as shown in block 126; and inserting new base calls, as shown in block 128. In one embodiment, assigning quality values comprises computing trace parameters, as shown in block 130, and obtaining quality values from a lookup table, as shown in block 134. Each of the actions comprising the method are discussed in more detail below.

In another embodiment, the second step may be thought of as base calling that includes refining original base calls and inserting new base calls. In this embodiment, refining base calls may include matching original base calls with peaks, re-calling unknown bases, and removing unmatched original bases.

D. Peak Processing
1. Peak Detection

Figure 4:
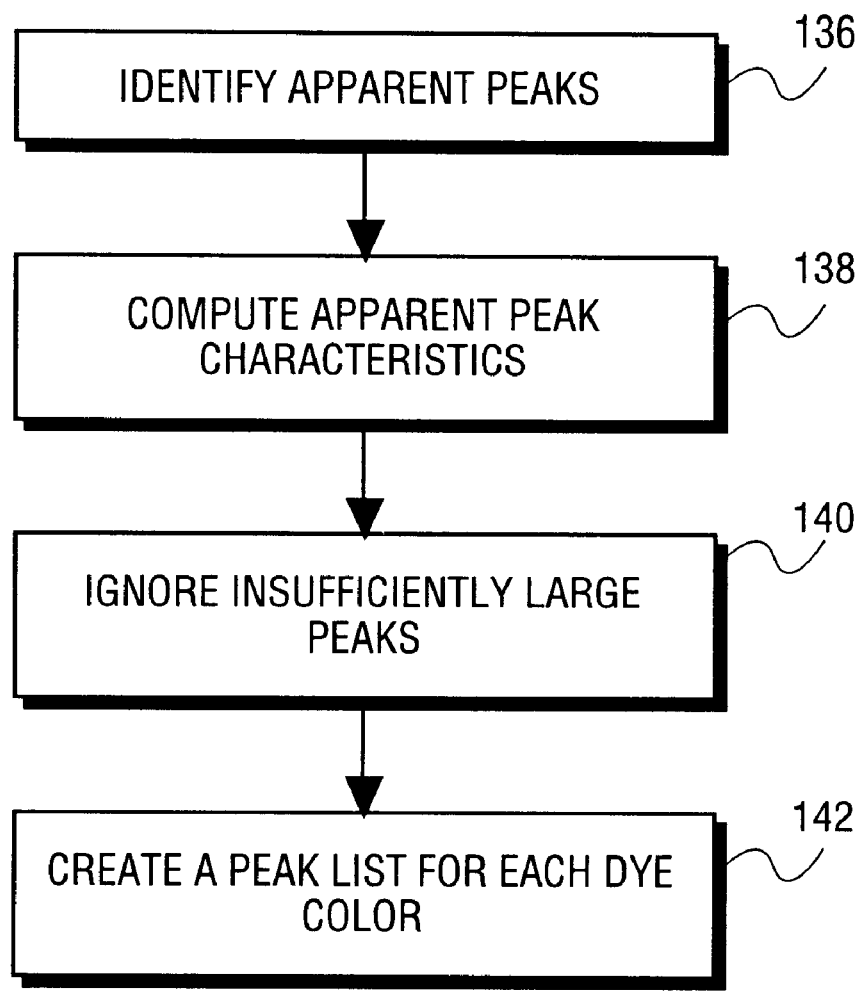
FIG. 4 depicts a flow of actions taken to detect peaks according to one embodiment of the method and system of the present invention.

FIG. 4 depicts a flow of actions taken to detect peaks according to one embodiment of the method and system of the present invention. Peaks in each of the four traces are detected by identifying all apparent peaks, as shown in block 136, computing apparent peak characteristics, as shown in block 138, ignoring insufficiently large peaks, as shown in block 140, and creating a peak list for each dye color, as shown in block 142. The traces corresponding to different dye colors are processed sequentially, one trace at a time.

To detect peaks in a given trace, inflection points are found by scanning the trace. An inflection point is the position in an electropherogram where the second derivative of the intensity of signal reverses sign. If $x[i]=i$ is the position of the $i^{th}$ data point in the electropherogram, and $y[i]$ is the intensity of signal at the position $x[i]$, then the second derivative of the signal intensity is computed as $y''[i]=y[i+1]-2*y[i]+y[i-1]$. A peak is determined to be the concave parts of the electropherogram located between the two inflection points: the left inflection point where $y''[i]$ turns negative, that is, $y''[i-1] \geq 0$ and $y''[i]<0$; and the right inflection point where $y''[i]$ becomes positive again, that is, $y''[i-1] \leq 0$ and $y''[i]>0$. Other portions of the electropherogram are not included as peaks at this stage of the analysis.

After peaks are detected, apparent peak characteristics are computed. These characteristics are used temporarily, because they are estimated using the observed or apparent signal, which is actually a sum of signals from individual peaks of the same dye color, and are therefore not very accurate. The apparent peak characteristics computed include width, area, height and spacing. Peak width is the distance between the peak beginning at the left inflection point and the peak end at the right inflection point. Peak area is the area below the peak. Peak position is the position in the electropherogram which bisects the peak area. Peak height is the signal at the peak position. Peak spacing is the distance between the positions of the current peak and the previous peak of the same dye color.

While detecting apparent peaks, lists of peaks of each color are simultaneously created. Each peak is modeled as a structure comprised of apparent peak characteristics. Each peak list is an array of peak structures. Small peaks are ignored and are not included in the list. A given peak i is considered small if it has an area that is equal to or less than 10% of the average area of 10 preceding non-truncated peaks included in the list, or if it has an area that is less than 5% of the area of the immediately preceding non-truncated peak. That is, $$a_i \leq 0.1 \bar{a}_{i-10 \ldots i-1} \text{ or } a_i < 0.05 a_{i-1}$$

where $a_i$ is the area of the $i^{th}$ peak.

2. Expansion of Peaks

Figure 5:
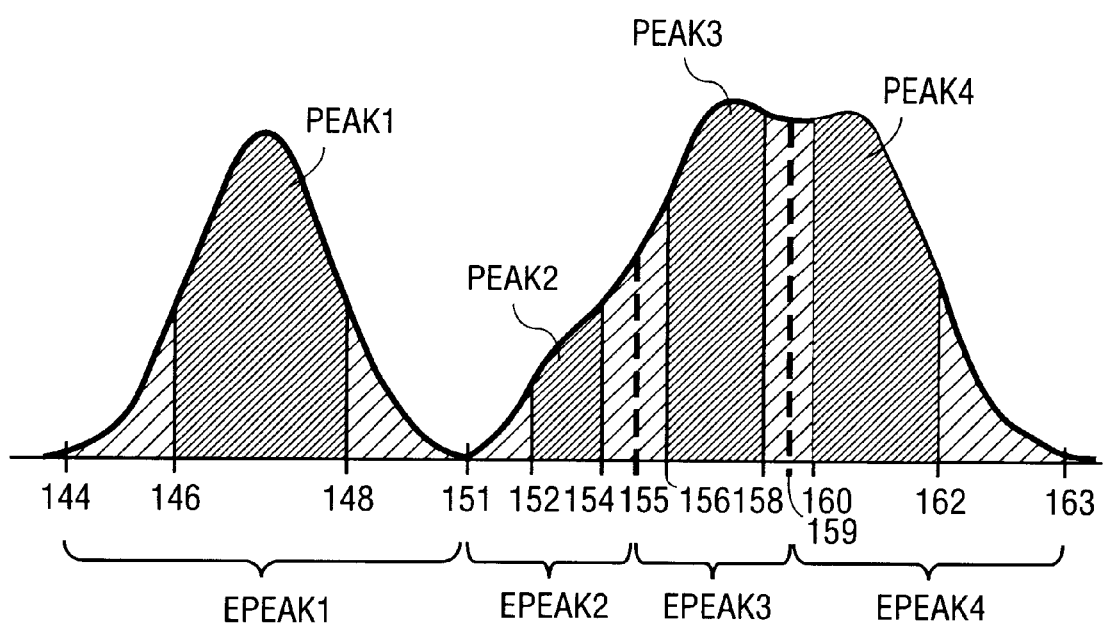
FIG. 5 depicts a sample electropherogram showing peaks and expanded peaks.

Detected peaks are subsequently expanded to include almost the entire electropherogram with non-zero signal, so that upon the expansion they look increasingly natural and their type, i.e., single and multiple, can be determined. In addition, expansion allows for later use of more data in analyzing the peaks. FIG. 5 depicts a sample electropherogram showing detected and expanded peaks. Detected peaks PEAK1, PEAK2, PEAK3, and PEAK4 are depicted within solid boundary lines. PEAK1 as initially detected is located between lines 146 and 148, PEAK2 as initially detected is located between lines 152 and 154, PEAK3 as initially detected is located between lines 156 and 158, and PEAK4 as initially detected is located between lines 160 and 162. After peak expansion, expanded peak EPEAK1 is located between lines 144 and 151, expanded peak EPEAK2 is located between lines 151 and 155, expanded EPEAK3 is located between lines 155 and 159, and expanded EPEAK4 is located between lines 159 and 163. After expansion, expanded peaks EPEAK2, EPEAK3 and EPEAK4 share boundaries 155 and 159 (shown as dashed lines).

Figure 6A:
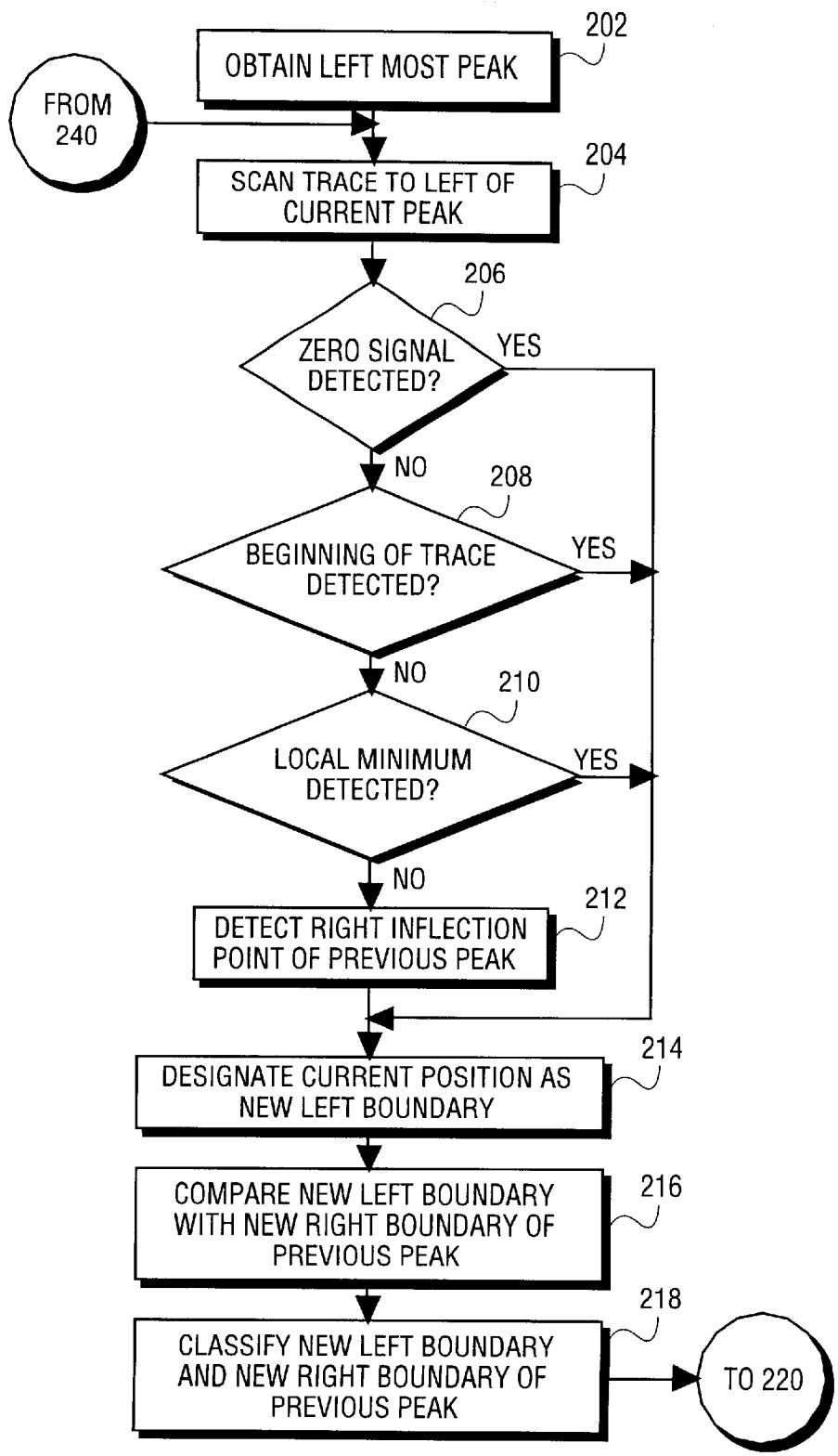
FIGS. 6A and 6B depict a flow of actions taken to expand peaks according to one embodiment of the method and system of the present invention.
Figure 6B:
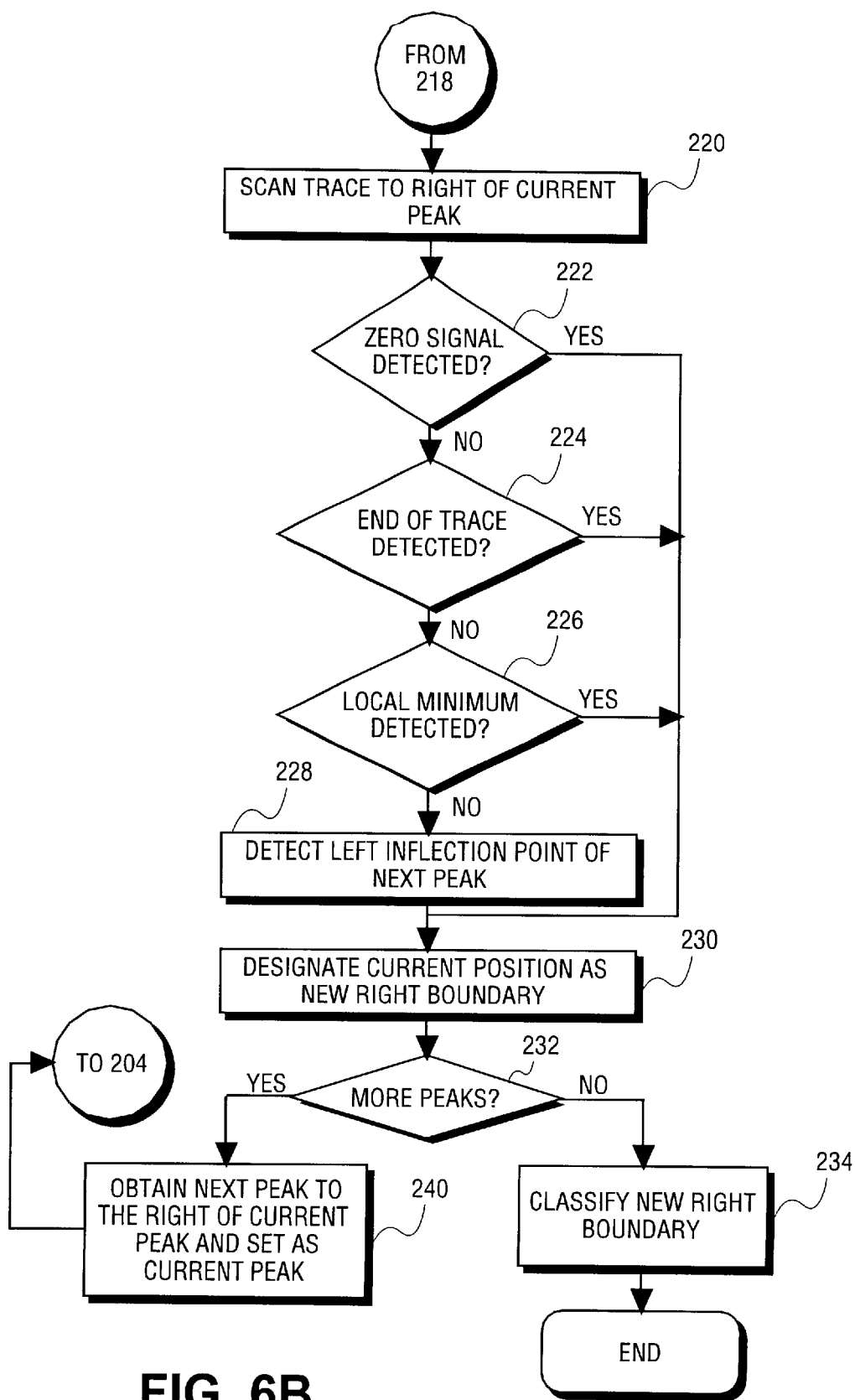

FIGS. 6A and 6B depict a flow of actions taken to expand peaks of the same dye color according to one embodiment of the method and system of the present invention. Peaks in the trace of a given dye color are processed sequentially, one peak at a time, starting from the leftmost peak. Referring now to FIG. 6A, the leftmost peak is obtained, as shown in block 202. The processing of each peak consists of three steps. In the first step, a trace adjacent to the detected peak is scanned, starting from the left inflection point to the left, toward the beginning of the trace, as shown in block 204. The scanning continues until any of the beginning of the trace, a zero value of signal intensity, a local minimum of signal intensity or the right inflection point of the previous peak is detected, whichever event occurs first, as shown in blocks 206, 208, 210 and 212. If a zero value of signal intensity is not detected, as shown in block 206, a check is made to determine if a local minimum of signal intensity is detected, as shown in block 210. If neither of these are detected, scanning continues until the right inflection point of the previous peak is detected, as shown in block 212. The position where the scanning stops is designated as the new left boundary of the current peak as shown in block 214.

In the second step, the new left boundary of the current peak is compared to the new right boundary of the previous peak, as shown in block 216. Based on this comparison, these boundaries are either accepted, or redefined. After that, both the boundaries are classified as one of three types, as shown in block 218. If the current peak is the leftmost peak in the list of peaks of a given color, then its new left boundary is accepted unconditionally and classified as a Type 1 boundary. If the current peak is not the leftmost peak, then the new left boundary is compared to the new right boundary of the previous peak. If the new left boundary of the current peak and the new right boundary of the previous peak coincide and the intensity of signal at each of these boundaries is less than 10% of the mean height of the current and previous peak, then both the new boundaries are accepted and classified as Type 1 boundaries. Examples of Type 1 boundaries are boundaries 144, 151, and 163 of FIG. 5. If the new left boundary of the current peak coincides with the new right boundary of the previous peak and the intensity of signal at any of these boundaries is greater than or equal to 10% of the mean height of the current and previous peak, then both the new boundaries are accepted and classified as Type 2 boundaries. Boundary 159 as shown in FIG. 5 is a Type 2 boundary. Finally, if the position of the new left boundary of the current peak is located to the left from the new right boundary of the previous peak, then both the new boundaries are redefined. The new positions of both the boundaries are set to the midpoint between the right inflection point of the previous peak and the left inflection point of the current peak. Both the boundaries are then classified as Type 3 boundaries. Boundary 155 is a Type 3 boundary, as shown in FIG. 5.

Referring now to FIG. 6B, in the third step, the trace adjacent to the detected peak is scanned, starting from the right inflection point, toward the end of the trace, as shown in block 220. The scanning continues until any of the end of the trace, a zero value of signal intensity, a local minimum of signal intensity or the left inflection point of the next peak is detected, whichever event occurs first, as shown in blocks 222, 224, 226 and 228. If a zero value of signal intensity is not detected, as shown in block 222, a check is made to determine if a local minimum of signal intensity is detected, as shown in block 226. If neither of these are detected, scanning continues until the left inflection point of the previous peak is detected, as shown in block 228. The position where the scanning stops is designated as the new right boundary of the current peak, as shown in block 230. A check is then made to determine whether there are more peaks remaining in the trace, as shown in block 232. If more peaks remain, the next peak to the right of the current peak is obtained and set as the current peak, as shown in block 240. Analysis then continues at block 204. If there are no further peaks, then the current peak is the rightmost peak in the list of peaks of a given color, and the new right boundary is accepted unconditionally and classified as a Type 1 boundary, as shown in block 234.

If after expansion a peak has new left and right boundaries of types "i" and "j", respectively, the peak may be referred to as a peak of Type "ij". For example, single peaks are peaks of Type "11". The first and the last peaks in a row of overlapping peaks are of the Types "1i" and "j1", respectively, where each of i and j is either 2 or 3. For example, referring to FIG. 5, EPEAK1 is a peak of Type 11, EPEAK2 is a peak of Type 12, EPEAK3 is a peak of Type 23, and EPEAK4 is a peak of Type 31.

When a peak's boundaries are expanded, all of the peak's apparent characteristics should be re-computed.

3. Resolving Multiple Peaks Into Intrinsic Peaks

Figure 7:
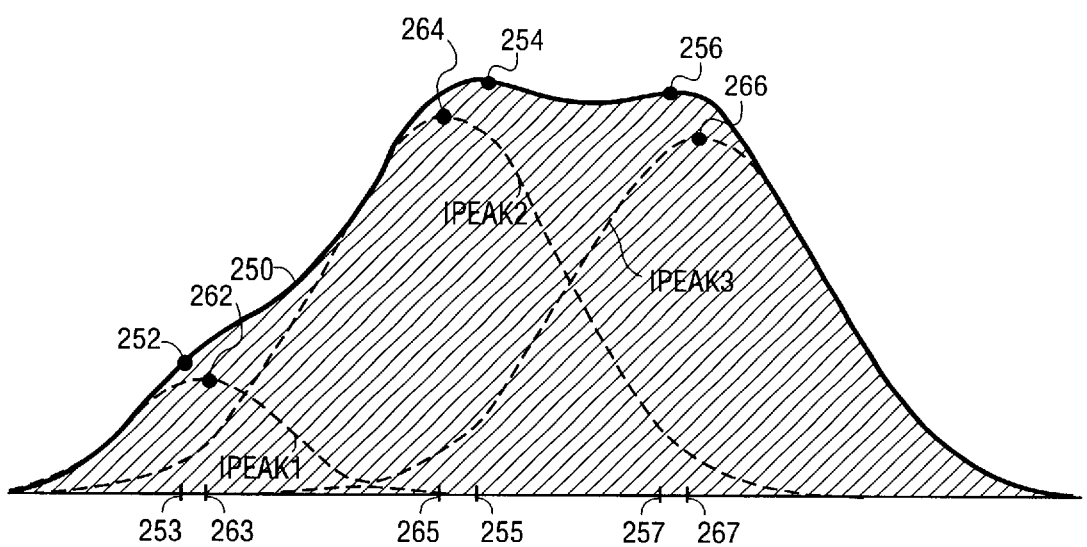
FIG. 7 depicts a sample electropherogram showing apparent peaks and intrinsic peaks.

As mentioned in the previous section, after expansion, overlapping peaks of the same color may not be separated and may share boundaries. Moreover, characteristics of overlapping peaks may still be inaccurate. For example, the height of a given expanded peak, defined as the signal at the peak position, may be inaccurate because it is estimated using the observed signal, which may actually include contributions from neighboring, overlapping peaks. According to the method of the present invention, this inaccurate height is regarded as the apparent height. FIG. 7 depicts a sample electropherogram showing apparent peaks and intrinsic peaks. The apparent electropherogram, 250, is determined to have three peaks with apparent peak heights 252, 254 and 256 and apparent peak positions 253, 255 and 257. It is these apparent peak heights and apparent peak positions that are used by prior art systems. To compute the intrinsic height of a peak, contributions from all the neighboring peaks to the signal at the peak position are subtracted. Similar adjustments are made to other apparent peak characteristics.

By definition, the intrinsic peak characteristics are measured from the data when no other peak of the same dye color is present in close vicinity of the current peak, thus eliminating any interference from surrounding peaks which plagues prior art methods. A mathematical model of peak electrophoresis is used to compute the expected shape of each peak. The shape is determined as a given function of three adjustable parameters. These parameters are computed for each peak by fitting a defined part of the electropherogram with the model. The resulting peak, having the expected shape and located at the expected position is called the intrinsic peak. Referring again to FIG. 7, the result in this example is the determination of three intrinsic peaks, IPEAK1, IPEAK2 and IPEAK3, with intrinsic peak heights 262, 264 and 266 and having intrinsic peak positions 263, 265 and 267. According to the method of the present invention, intrinsic peak characteristics are used in subsequent processing. This is an improvement over prior art systems, all of which use apparent peak characteristics in base calling and error probability calculations.

a. Mathematical Model of a Peak Shape

A simple model is used for peak electrophoresis. The model describes the evolution of a peak while the DNA sample moves through an electrophoretic cell. The model takes into account two physical processes: first, electromigration of DNA fragments with velocity v under an applied electric field; and, second, Brownian diffusion of the molecules of the fragments with diffusion coefficient D. Electromigration is responsible for the translation of a peak in an applied field without changing the shape of the peak, while diffusion results in evolution of the peak shape. A rectangular peak of a finite width is used as an initial condition. The shape of the peak observed in an electropherogram is assumed to be the result of evolution in a time it took the peak to pass through an electrophoretic cell.

The mathematical model of peak electrophoresis is represented by:

$$\frac{\partial C}{\partial t} = -v \cdot \frac{\partial C}{\partial x} + D \frac{\partial^2 C}{\partial x^2} \qquad \text{Equation (1)}$$

This equation is a one-dimensional differential equation of the convective diffusion type. In this equation, t represents time, x represents the position in the electrophoretic cell which is roughly proportional to the position in the electropherogram, and C is the local concentration of the considered type of DNA subfragments, which is proportional to the intensity of signal produced by the subfragments. The minus sign before v signifies that the subfragments are assumed to migrate from the left to the right, that is, in the positive direction of x.

Equation (1) ignores a number of physical phenomena accompanying electrophoresis, such as the effect of the DNA subfragments (which are charged molecules) on the local conductivity of the medium and the interaction of the DNA fragments with buffer electrolyte, the low molecular weight ions which are also present in the electrophoretic cell. Even so, the approximations, work well when the concentration of the DNA fragments is much less than the concentration of the buffer electrolyte.

A reasonable initial distribution for the DNA fragments is the rectangular profile of height $C_0$ and width $2w_0$ centered at the position x=0:

$$t = 0; \quad C(x, 0) = \begin{cases} 0, & x < -w_0; \\ C_0, & -w_0 \leq x \leq w_0; \\ 0 & x > w_0. \end{cases} \qquad \text{Equation (2)}$$

A solution to Equations (1) and (2) is given by $$C(x, t) = \frac{1}{2} C_0 \cdot \left[ Erf\left(\frac{w_0 - x + vt}{2\sqrt{Dt}}\right) + Erf\left(\frac{w_0 + x - vt}{2\sqrt{Dt}}\right) \right] \qquad \text{Equation (3)}$$

where Erf(z) is the error function, $$Erf(z) = \frac{2}{\sqrt{\pi}} \int_0^z e^{-z^2} dz.$$

This solution, Equation (3), describes the displacement of the peak at constant velocity v in the direction of positive x accompanied by evolution of the peak shape as the result of the Brownian diffusion of DNA fragments in the peak. At any time t, the peak shape remains symmetric. The symmetry of the peak shape is the consequence of the assumptions that the original peak shape at the time t=0 is symmetric and that the interaction of the DNA with each other and with the buffer electrolyte may be ignored. In practice, the observed analyzed peaks are slightly asymmetric, which may be the result of the asymmetry of an initial distribution of subfragments, which is not accounted for by Equation (2), or of physical processes ignored by the model, or even the result of distortion of the data as analyzed by the original signal processing system, such as, for example, the ABI Base Caller. Nevertheless, Equation (3) provides a good first approximation.

b. Fitting a Single Peak

To fit a single expanded peak, it is assumed that its position, $x_0=vt$, may be determined from the electropherogram, and the origin of the new reference frame is placed at this position. Thus, $$C(z,t) = \frac{1}{2} C_0 \cdot \left[ Erf\left(\frac{w_0 - z}{2\sqrt{Dt}}\right) + Erf\left(\frac{w_0 + z}{2\sqrt{Dt}}\right) \right] \quad \text{Equation (4)}$$

The coordinate, z, in the new reference frame is defined by $z=x-x_0$, and the peak shape in the new coordinate system is symmetric with respect to the origin z=0. Equation (4) depends on three parameters: $C_0$, $w_0$ and $\beta=(Dt)^{1/2}$. If these parameters, together with the peak position $x_0=vt$, are estimated by fitting the data, then the intrinsic peak will be uniquely defined. To estimate the three parameters $C_0$, $w_0$ and $\beta$, three measurable characteristics of a peak are needed. The three characteristics are: peak area, S, peak height, H; and peak width, W, defined as a width at the height H/2. Once these characteristics are computed from the data, the parameters $C_0$, $w_0$ and $\beta$ for a given single peak are estimated using the following set of three nonlinear equations:

$$H = C_0 \cdot Erf\frac{w_0}{\beta} \quad \text{Equation (5)}$$

$$S = 2w_0 \cdot C_0 \quad \text{Equation (6)}$$

$$Erf\left(\frac{w_0 - W/2}{\beta}\right) + Erf\left(\frac{w_0 + W/2}{\beta}\right) = Erf\left(\frac{w_0}{\beta}\right) \quad \text{Equation (7)}$$

Although single peaks fit relatively accurately, the fit is not perfect. The method of the present invention uses best-fit parameters $C_0$, $w_0$ and $\beta$, to compute a peak resolution. Peak resolution is a measure of deviation of the model from the data. Peak resolution is later used for both base calling and computing quality values. The peak resolution is computed by determining the curve which describes the absolute difference between the model signal, given by Equation (4), and the data, i.e., the observed signal in the trace. This absolute difference curve is a function of the position in the electropherogram and is defined between the apparent beginning and apparent end of the expanded apparent peak. The peak resolution is computed as the ratio of the area under the absolute difference curve to the area of the expanded apparent peak. Thus, the peak resolution is always non-negative and equals zero if and only if the model ideally fits the data. Normally, the value of peak resolution is less than unity. For peaks that are fit well, peak resolution is typically approximately 0.1 or less.

C. Resolving Multiple Overlapping Peaks

Because the model shape of each peak depends on three adjustable parameters, to fit a group of n overlapping peaks, 3n independent parameters describing the shapes of intrinsic peaks, plus n parameters describing their positions are adjusted simultaneously. Experience indicates that, in some cases, n may be as high as 10 at the end of trace. The computational complexity of this problem may be reduced by exploiting specific properties of the physical model. Two of the three parameters of the peak shape are local invariants. That is, two of the three parameters are assumed to share the same values as neighboring peaks in the trace. These invariant parameters are: $w_0$ and $\beta$.

Parameter $w_0$ is the half-width of the original volume where all the DNA fragments were placed before the start of the electrophoresis experiment. Parameter $\beta=(Dt)^{1/2}$ is also expected to remain the same for neighboring peaks. This is because such peaks spend about the same t in the electrophoretic cell, and because the diffusion coefficient D of the subfragments located in these peaks are expected to be about the same. Since $w_0$ and $\beta$ are the local invariants, it follows from Equations (5), (6) and (7) that the measurable peak characteristics S/H and W are also local invariants. To fit n overlapping peaks of the same color, these invariants are used in a sequence of computations.

In one embodiment, the average values of S/H and W are computed among five good immediately preceding apparent peaks. The peak is regarded as good if it is Type 11, 12 or 21 (according to the peak types discussed above), and it has a peak resolution of 0.2 or less. If the peak type is 12, the left half of the peak is used to compute S and W, and the result is doubled. If the peak type is 21, the right half of the peak is used to compute S and W, and the result is doubled.

From these average values, the shape parameters $w_0$ and $\beta$ are computed using Equations (5), (6) and (7) and assigned to all the overlapping peaks in the group. For each peak in the overlapping group, the rest of the peak parameters, the initial height $C_0$ and the intrinsic peak position, ipos, are computed via an iterative procedure. First, a zero-order approximation for these parameters is chosen. In this computation, the zero order approximation for $C_0$ is referred to as $C_0^{(0)}$ and the zero order intrinsic position is referred to as ipos$^{(0)}$. $C_0^{(0)}$ is computed as $C_0^{(0)}=H/Erf(w_0/\beta)$, where H is the apparent height of the expanded peak, and ipos$^{(0)}$ is set to the apparent position of the peak. The next order approximation for parameters $C_0$ and ipos of each peak in the group is then computed by processing all the peaks of the group sequentially in one pass from the left to the right. To compute the next order approximation for parameters $C_0$ and ipos of a given peak, the intrinsic signals of all other peaks are subtracted from the original data signal corresponding to the n peaks. The resulting signal is used to determine the next order approximation for $C_0$ and ipos. Specifically, ipos$^{(1)}$ is set to the position of maximum of the resulting signal and $C_0^{(1)}$ is set to the ratio of the maximum value of the resulting signal to $Erf(w_0/\beta)$. In one embodiment, this next order computation is repeated four times.

E. Refining Base Calls

After peaks have been processed such that intrinsic peak characteristics have been determined, original base calls are refined. Base call refining comprises determining which of the peaks correspond to real bases of the DNA fragment, sorting out noise peaks, and inferring the DNA sequence.

Figure 8:
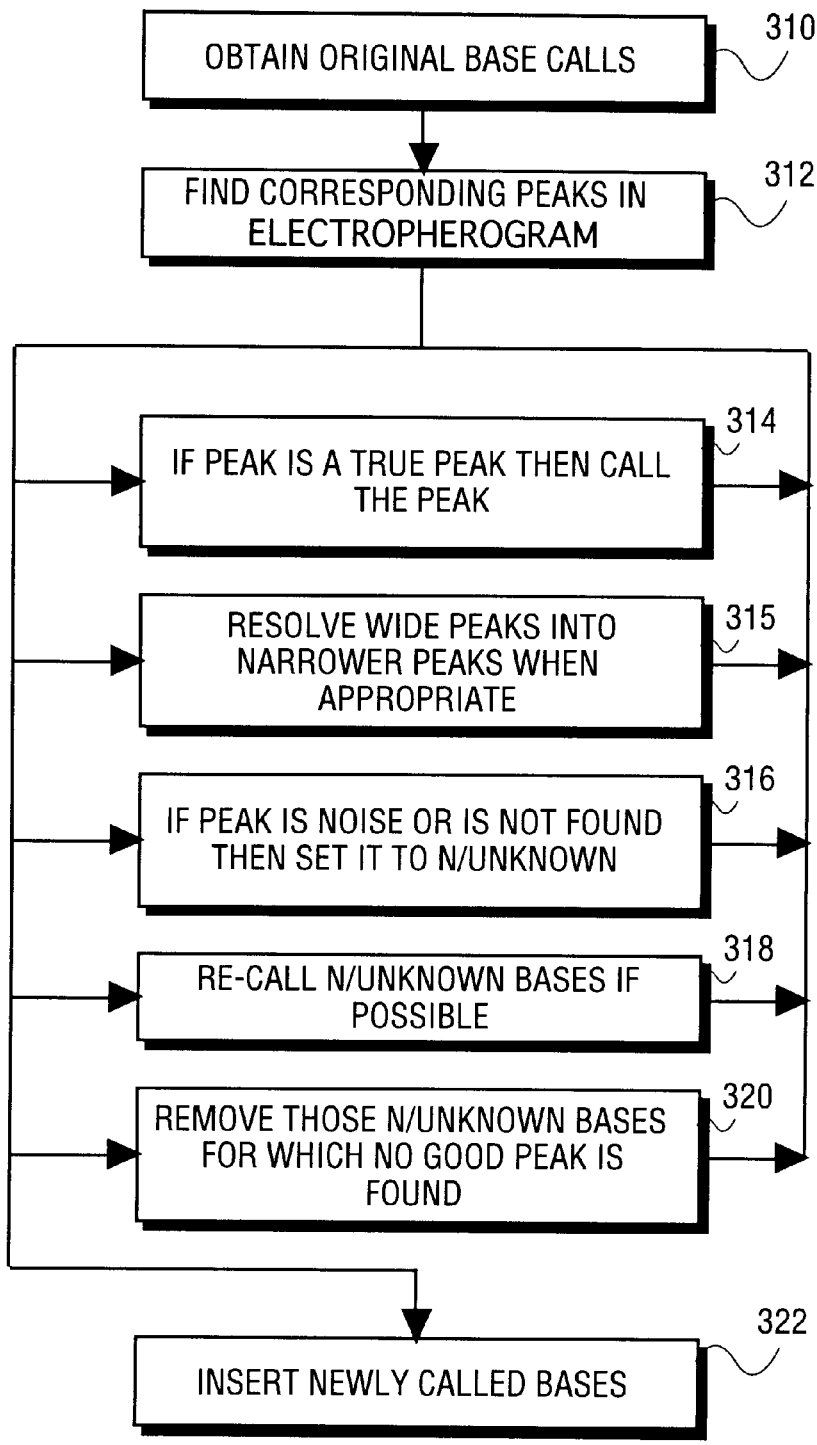
FIG. 8 depicts a flow of actions taken to refine original base calls according to one embodiment of the method and system of the present invention.

FIG. 8 depicts a flow of actions taken to refine base calls according to one embodiment of the method and system of the present invention. In one embodiment, data from a base calling system, such as the ABI Base Caller, are used to obtain a trace and make a first try at calling bases. These called bases, the original base calls, are obtained from a sample file along with other data as an input, as shown in block 310. These original base calls are regarded as a first-order approximation to the true DNA sequence. The original base calls are then edited or refined. This refining may also be referred to as re-calling as the originally called bases are called again for a second time. For each original base call, the corresponding peak in the electropherogram is searched at the location in the trace corresponding to the original base call, as shown in block 312. If the peak is found, and the peak is a the true peak, the peak's base is called, as shown in block 314. When appropriate, wide peaks are resolved into narrower peaks, as shown in block 315. If a peak is determined to be noise or is not found, it is called as N or unknown, as shown in block 316. All base calls labeled as unknown or N are then analyzed, and a best guess is used to replace Ns by one of 'A', 'C', 'G' or 'T'. Unknown bases are either re-called, as shown in block 318, or rejected. If no appropriate peak is found at or near the unknown base location, those unknown bases for which no good peak is found are removed, as shown in block 320. Newly added base calls may then be inserted into the original base call sequence, as shown in block 322.

1. Refining Original Base Calls

The sequence of bases called by the original base calling system, including unknown or N bases, is refined. A peak corresponding to a given base is determined using the original base call location from the sample file together with other data.

a. Known Original Bases

Figure 9:
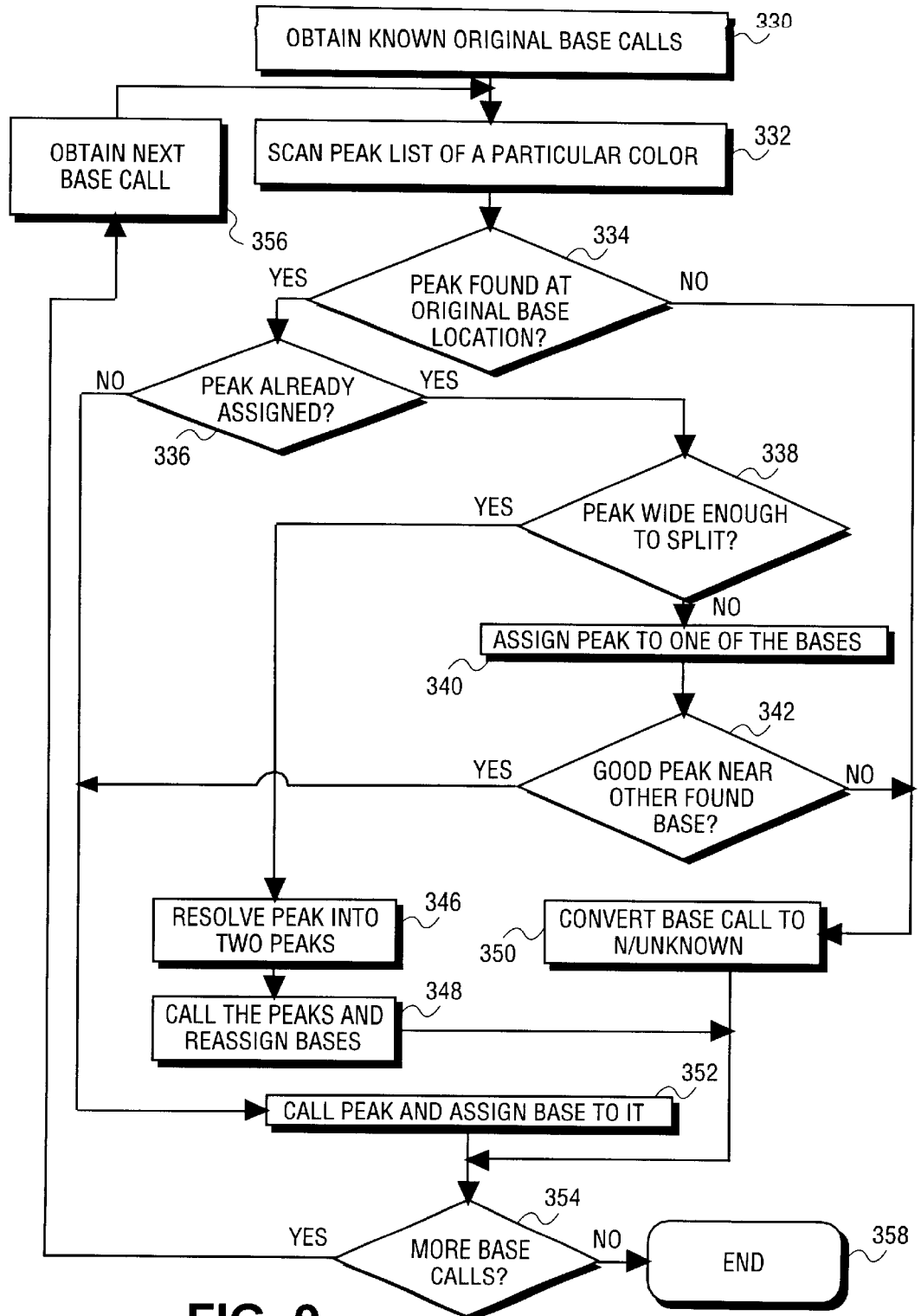
FIG. 9 depicts a flow of actions taken to refine originally called and known bases according to one embodiment of the method and system of the present invention.

FIG. 9 depicts a flow of actions taken to refine originally called and known bases according to one embodiment of the method and system of the present invention. Original known base calls are obtained, as shown in blocks 330. Then, the peak list for one of the four particular colors representing A, C, G and T is scanned sequentially, starting from the peak having the smallest location index, as shown in block 332. For each original base that is known, that is, it was originally designated as A, C, G or T, the list of peaks of the color corresponding to the base is searched for a peak such that the original base location falls into the peak area, as shown in block 334. That is, a check is made to determine whether a peak in which the original base location falls between the beginning and end of the peak is found.

If a peak is found, as shown in block 334, a check is made to determine whether the peak has already been assigned, as shown in block 336. That is, a check is made to determine if any of the previously considered bases had a location falling into the peak's area. If the peak has not already been assigned, as shown in block 336, then the peak is called and the base is assigned to it, as shown in block 352. More specifically, the base is accepted as called, the peak is marked called, and the base location is reset to the intrinsic position of the called peak.

If no peak is found at the location of the original base, as shown in block 334, then the base is set as N so that it will be reconsidered in later processing, as shown in block 350.

If a peak corresponding to the current original base is found, as shown in block 334, referred to as the second base, and the peak was already called and assigned to another base, as shown in block 336, referred to as the first base, that is, one of the previously refined bases had an original location falling into the peak's area, then a determination is made whether the peak is wide enough to be split into two good peaks, as shown in block 338. If the peak is truncated, it will be considered wide enough to split. A peak is considered truncated when the data signal of the peak reaches the maximum value of the signal detected for the trace. If the peak is not truncated, then to determine whether a peak is wide enough to split, the ratio of the apparent peak area (computed earlier when expanding peaks) to the intrinsic peak height is computed. This ratio is compared to the similar ratio averaged among five immediately preceding good peaks. If the computed ratio is greater than the average ratio multiplied by the factor 1.125, then the peak is wide enough to split. The factor 1.125 has been determined empirically through optimization of the base calling accuracy. If a peak is wide enough, it is resolved into two peaks, as shown in block 346, and the two peaks are called and the two bases are reassigned, as shown in block 348. That is, each of the two bases, the first base and the second base, is assigned to one of the two newly resolved peaks, the original peak is removed from the list of peaks of this trace, and the two new peaks are inserted into this list.

If the peak is not wide enough to split, as shown in block 338, that is, if the computed ratio is not greater than the average ratio multiplied by this factor, the peak will not be resolved into two peaks. One of the two bases, the first base and the second base, is assigned to this peak, as shown in block 340. Specifically, the two original base locations are compared to the peak position. Whichever base is located closer to the peak position is assigned to the peak. If the two original base locations are equidistant from the peak position, then the one that is located where the signal is stronger is selected. As to the other base, the location of the previous and next base in the trace corresponding to the current base is searched in an attempt to find a good peak. That is a check is made to determine whether there is a good peak near the other found but, as yet, unassigned base, as shown in block 342. If no good peaks are found near the other base, the base is set as unknown or N so that it is considered in later analysis, as shown in block 350. If a good peak is found near the other base, the peak is called and the base is assigned to it, as shown in block 352.

A check is then made to determine whether there are more known original base calls, as shown in block 354. If there are more, then the next original base call is obtained, as shown in block 356, and execution continues at block 332. If there are no further original base calls, then this portion of the processing ceases, as shown in block 358.

b. Unknown Bases

Figure 10:
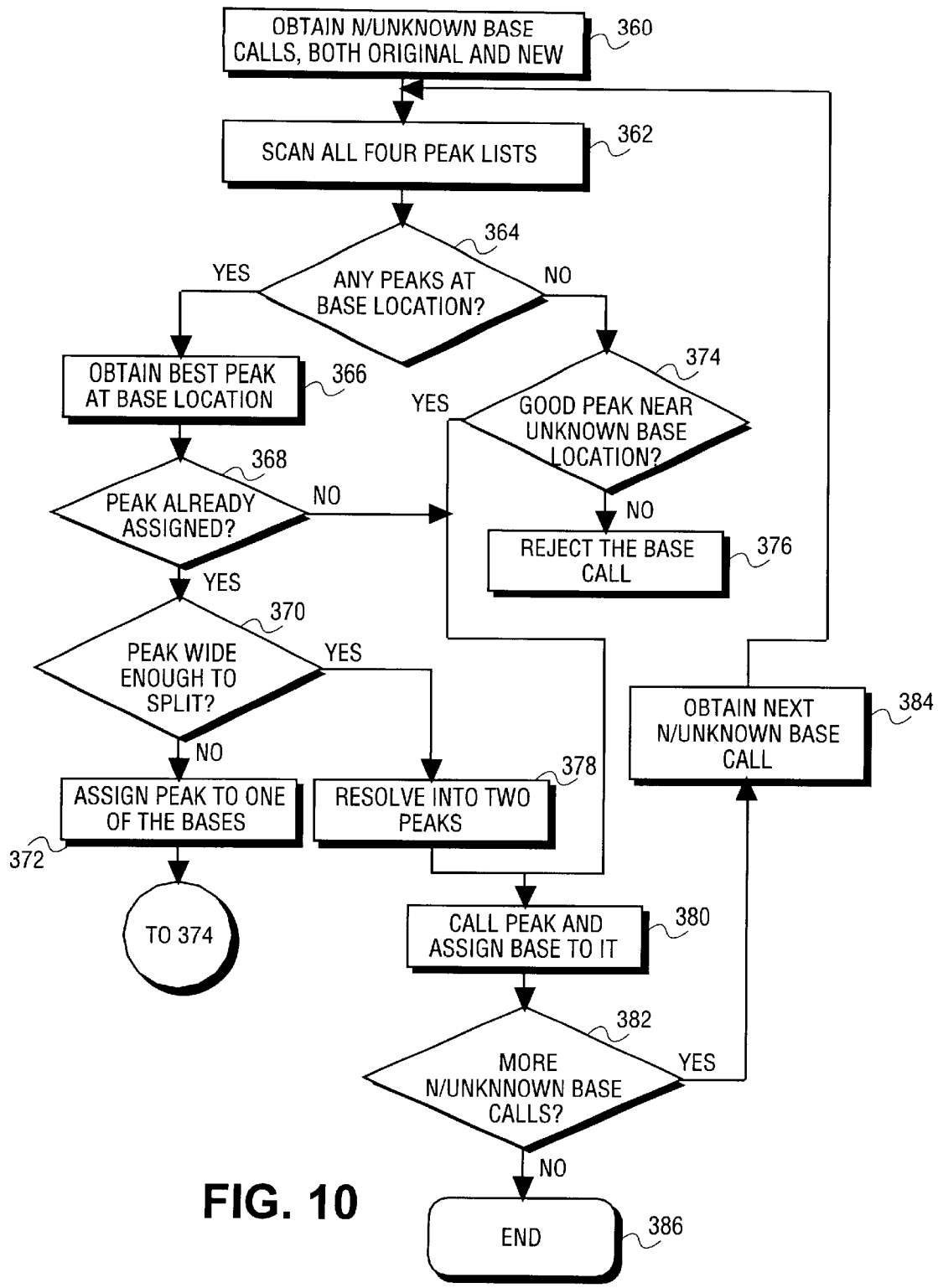
FIG. 10 depicts a flow of actions taken to refine base calls designated as unknown or N according to one embodiment of the method and system of the present invention.

FIG. 10 depicts a flow of actions taken to refine base calls designated as unknown or N according to one embodiment of the method and system of the present invention. Those bases designated as unknown or N, both originally and during refining of original base calls, are processed. More specifically, the bases designated as unknown or N when refining the original base calls as well as the bases that were originally located but designated as unknown or N by the original base calling system are analyzed in an attempt to refine or recall them to a best guess. The unknown or N base calls are obtained, as shown in block 360. The peak lists containing data for all four traces A, C, G and T are scanned, as shown in block 362. A check is made to determine whether there are is an uncalled peak at the location of the unknown base, as shown in block 364. If there are no peaks at the base location, a check is then made to determine whether there are any peaks in any of the four traces near the unknown base location, as shown in block 374. If there are no good peaks near the unknown base, the unknown base call is rejected, and it is removed from the list of called bases, as shown in block 376.

If there are one or more peaks found at the base location, the best peak and its trace are selected at the base location, as shown in block 366. This selection is made according to the following rules:

- a non-truncated peak is preferred over a truncated peak;
- among non-truncated peaks, only those peaks having a peak resolution parameter of 0.2 or less are considered;
- between two non-truncated peaks, their intrinsic height is compared and the peak with the greater height is selected; and
- among two truncated peaks, the wider peak is selected.

After a best peak is found, a check is made to determine if this peak was already assigned, that is, was called previously, as shown in block 368. If the peak was not previously called, the peak is called, and the base is assigned to it, as shown in block 380. More specifically, the peak is marked called and the unknown designator or N is replaced with the base corresponding to the best peak.

If the peak was already assigned to another base, a check is made to determine if the peak is wide enough to split, as shown in block 370. This analysis is the same as that discussed above regarding block 338. If the peak is wide enough to split, the peak is resolved into two peaks, as shown in block 378, and then the peak is called and the base is assigned to it, as shown in block 380. More specifically, the original peak is removed from the peak list corresponding to the trace, each of the two new peaks are marked called, each of the new peaks are inserted into the peak list, the current base and the previously called base are assigned to one of the descendant peaks, and the unknown designator or N is replaced with the base corresponding to the assigned peak. In one embodiment, if the best peak is too narrow, the base may be left as is and may be processed in a subsequent step. If the peak is not wide enough to be split, the peak is assigned to one of the two bases, as shown in block 372. Processing then continues at block 374 as discussed above.

If a peak is not found at the unknown base location, but a good peak is found near the unknown peak, then the peak is called and the base is assigned to it, as shown in block 380. More specifically, the peak is marked called, the unknown designator or N is replaced with the base corresponding to the trace of the near peak, and this base is assigned to the peak. A check is then made to determine if there are any further unknown or N base calls to be refined, as shown in block 382. If there are more, the next unknown or N base call is obtained, and processing continues at block 362. If there are no further unknown or N base calls to process, the processing ceases at block 386.

2. Inserting New Base Calls

All the peaks, both called and uncalled for all colors are then reviewed, and some previously uncalled peaks are called.

a. Creating a Multi-Colored Ordered List of All Peaks

Before reviewing all the peaks, a single mixed list of peaks of all colors is created from the four uni-colored peak lists that existed up to this point. To create the single list of peaks, each of the four uni-colored peak lists is scanned simultaneously starting from peaks with lower peak positions. Peaks are selected for the single list according to the following rules:

- peaks having lower intrinsic positions are selected before other peaks;
- if two or more peaks from different traces are found which have the same positions, called peaks are placed before uncalled peaks;
- if two or more peaks from different traces have the same positions and all are called, the peak having a lower index in its corresponding uni-colored peak list is placed first;
- if two or more peaks from different traces have the same positions and all are uncalled, the peak with the greater intrinsic peak height is placed first;
- if two or more peaks from different traces have the same positions, and all are uncalled, and all have the same intrinsic peak height, then the peak with greater area is placed first.

b. Checking the Peak Calling Criteria and Calling Good Peaks

Figure 11:
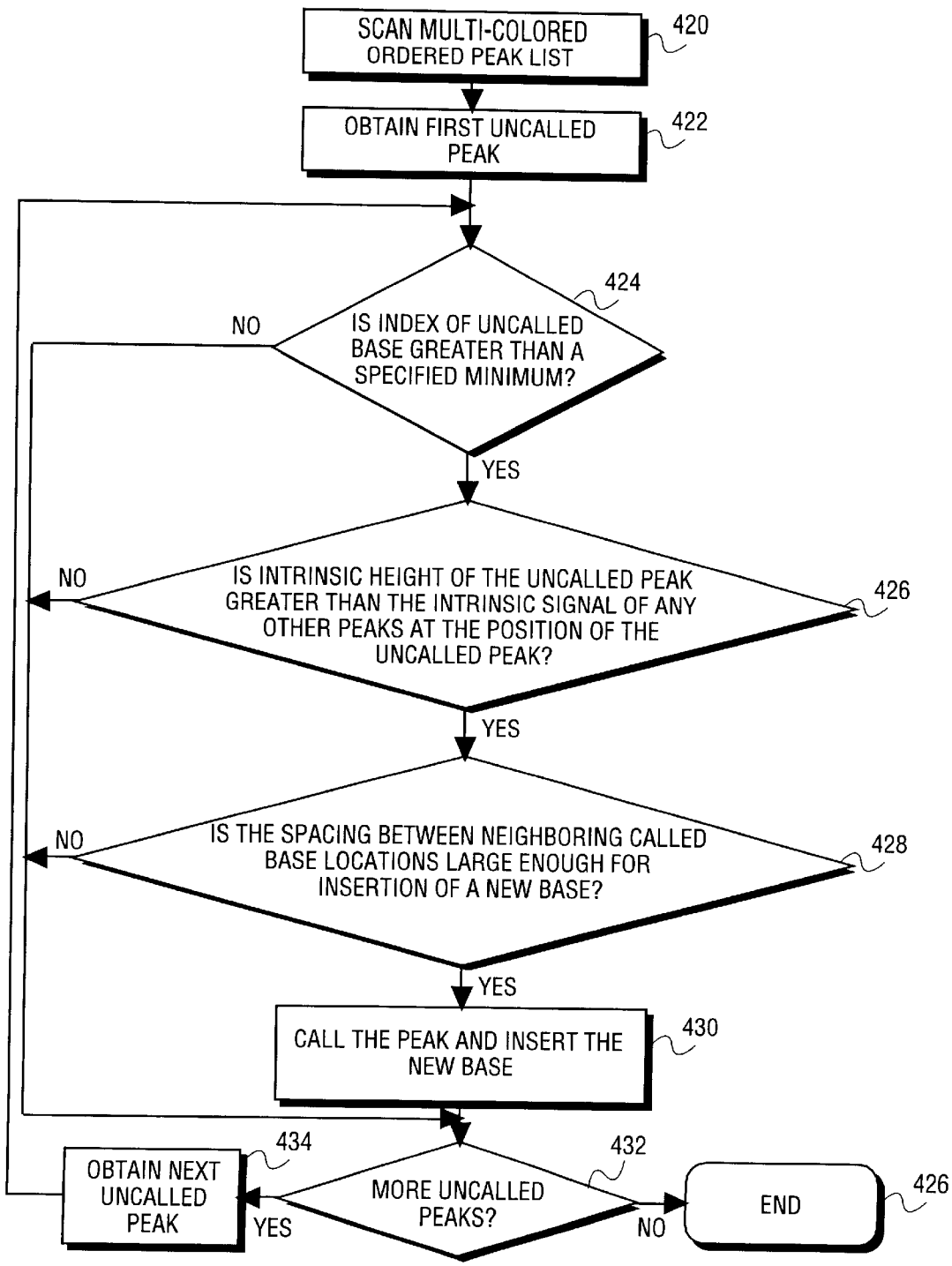
FIG. 11 depicts a flow of actions taken to call uncalled peaks according to one embodiment of the method and system of the present invention.

FIG. 11 depicts a flow of actions taken to call uncalled peaks according to one embodiment of the method and system of the present invention. In this, the last step in the base calling analysis, the single multi-colored peak list is scanned, as shown in block 420, in an effort to locate good but uncalled peaks. Each successful peak candidate will satisfy a multitude of requirements. By definition, the peak must not have been previously called in an earlier portion of the analysis. The peak must not be not truncated. When the first uncalled peak is obtained, as shown in block 422, at least three analyses are performed. Each of the analyses is made in succession; if any of them fail, no further checks are made, and the peak is not called.

First, a check is made to determine whether the base index, which is the index of the base which would be inserted into the called base sequence if the peak would be called, is greater than a system specified recommended minimum. In one embodiment, this minimum is set to 600. A check is then made to determine whether the intrinsic height of the uncalled peak is greater than the intrinsic signal of any other peak at the location corresponding to the candidate peak's position, as shown in block 426. Last, a check is made to determine whether the spacing between neighboring called base locations is large enough for insertion of a new base, as shown in block 428. That is, a check is made to determine if the spacing between neighboring called base locations is sufficiently larger than the average spacing of preceding bases. More specifically, the distance in the electropherogram between the positions of the two called peaks, the one immediately preceding and the other immediately following the current peak candidate, must be no less than the average peak spacing among the 10 immediately preceding called peaks multiplied by the peak insertion factor, PIF, which is computed as:. Last, a check is made to determine whether the spacing between neighboring called base locations is large enough for insertion of a new base, as shown in block 428. That is, a check is made to determine if the spacing between neighboring called base locations is sufficiently larger than the average spacing of preceding bases. More specifically, the distance in the electropherogram between the positions of the two called peaks, the one immediately preceding and the other immediately following the current peak candidate, must be no less than the average peak spacing among the 10 immediately preceding called peaks multiplied by the peak insertion factor, PIF, which is computed as:

$$PIF = \begin{cases} \infty, & \text{base\_index} \leq 600 \\ 2 - 1.1 \cdot (\text{base\_index} - 600)/200, & 600 < \text{base\_index} \leq 800 \\ 0.9 & \text{base\_index} > 800 \end{cases}$$

When peaks meeting each of these criteria are found, the peaks are called and corresponding new bases are inserted into the called base sequence, as shown in block 430. A check is then made to determine if there are any further uncalled peaks, as shown in block 432. If there are more uncalled peaks, the next uncalled peak is obtained, as shown in block 434, and processing continues at block 424. If thee are no further uncalled peaks, the processing ceases at block 436.

F. Quality Value Assignment

Quality values are then assigned to the called bases. Trace parameters and a lookup table are used to compute quality values. The quality value, QV, for a given called base position is defined as:

$$QV = -10 \cdot \log P$$

rounded to the nearest integer. Here, P is the probability of error in base calling at this position. To be able to successfully compute the QVs, the system trains on data for which the correct base sequence is already known. By comparing this correct sequence with what the system outputs, the base positions at which the system makes base calling errors are identified. These base positions are stored by training software together with the "conditions" in the trace (represented by trace parameters) under which the error was made. Using these data and a dynamic programming code, which is also a part of the raining software, values of the four trace parameters are then mapped to a quality value. This map is saved in a file called the "lookup table". The lookup table is used when assigning quality values. To determine the quality value for a given base, the four trace parameters for the base are computed from the electropherogram. The lookup table is then consulted.

1. Computing Trace Parameters

The system involves four trace parameters. All of these trace parameters involve intrinsic peak characteristics. Three of the trace parameters, the two peak height ratios and the peak spacing ratio, are similar to those used in Phred, but in the method of the present invention these trace parameters are derived from intrinsic, rather than apparent peak heights and positions. The fourth trace parameter is peak resolution. This parameter was defined above. Peak resolution as defined and used herein has nothing in common, except its name, with Phred's peak resolution parameter.

Two peak height ratios, phr3 and phr7, are used as trace parameters. To compute phr3, a window of three called peaks in the electropherogram, centered at the current called peak is selected. The ratio of the intrinsic height of the largest uncalled peak in the window and the lowest called peak defines phr3. If there are no uncalled peaks, the largest of the three uncalled trace array values at the location of the called base is used instead. Trace parameter phr7 is computed similarly, but with a window of seven called peaks. To compute the peak spacing ratio, psr7, a window of seven called peaks in the electropherogram, centered at the current called peak, is selected. The ratio of the largest peak-to-peak spacing in the window to the smallest peak-to-peak spacing is then calculated. Only called peaks are considered when computing psr7 and the spacing is defined as the distance between the positions of adjacent called peaks. The definition of the peak resolution parameter, pres, is as set forth above. In one embodiment, pres is a double precision value.

2. Obtaining Quality Values

After the four trace parameters $phr3_0$, $phr_0$, $psr7_0$ and $pres_0$ for a given called base calculated, the lookup table is consulted to estimate the quality value of the base. In one embodiment, the lookup table consists of five columns. The first column contains (integer) quality values. Each of the four other columns contains double precision threshold values for the trace parameters $phr3_T$, $phr7_T$, $psr7_T$ and $pres_T$, The lookup table is scanned line by line, starting from the first line, until a line satisfying the following conditions is found:

$phr3_0 \leq phr3_T$; $phr7_0 \leq phr7_T$; $psr7_0 \leq psr7_T$; $pres_0 \leq pres_T$.

The quality value from the first column of this line is assigned to the base. Upon finding such a line, scanning of the lookup table is terminated.

G. Training the System

To successfully implement and use the system and method of the present invention, the system must be calibrated by training the system. The training procedure consists of two major steps: first, a training data file is generated by extracting and storing information from sample files and a consensus sequence; and, second, a lookup table is generated using the extracted information. As such, training receives as input a set of sample files also known as a dataset, and the correct target sequence, also known as the consensus sequence. The dataset may consist of from a few hundred to a few thousand sample files. The consensus sequence may be over 100,000 bases long. Instead of a single consensus sequence, a plurality of consensus sequences, each matching a given subset of fragments, may be passed as an input to the training software.

At the extraction and storing step, the method begins by processing electropherograms for each fragment, determining the called sequence of the fragments' bases, and computing trace parameters for each called base. The method then determines which part of each fragment is actually relevant to the consensus sequence. This is achieved by a local alignment of the called fragment with the consensus sequence. Only those bases corresponding to the relevant part of the fragment are used in the training process. The computed result for each "good" base is then stored in an ASCII data file, which may be referred to as a training file. The training file contains the information about the values of four trace parameters for each good base, the location index of the base in the fragment and consensus sequence, and whether the base call was correct.

At the second step, a lookup table is generated. According to one embodiment of the method, information is read from the training file. A binning procedure for each of the four trace parameters is then performed in which the good bases are partitioned into a specified number of subsets which may be referred to as bins. Each bin contains only the bases for which the given trace parameter lies within certain limits, called thresholds. The values of the thresholds are selected and computed so that each bin contains roughly the same number of bases. The total number of thresholds for a given trace parameter is, therefore, equal to the specified number of bins plus one. A lookup table is then generated. The lookup table comprises a plurality of lines. Each line contains four parameter thresholds, together with a quality value corresponding to those thresholds. Multiple lines may have the same quality value.

1. Generating a Training File

To generate a training file, peaks are processed and bases are called as discussed above. After bases in the fragment are called, the next step is to determine which part of the fragment is actually relevant to the consensus. This is done by aligning the called fragment with a corresponding consensus sequence and finding the region of their local alignment. To this end, a FASTA algorithm (W. R. Pearson and D. J. Lipman D. J., "Improved Tools For Biological Sequence Analysis", *Proceedings of the National Academy of Sciences of he USA*, vol. 85, pp.2444–2448 (1988)) and a linear Smith-Waterman (SW) algorithm (T. F. Smith and M. S. Waterman, "Identification Of Common Molecular Subsequences", *Journal of Mathematical Biology*, vol.147, pp.195–197 (1981)) may be implemented. The FASTA algorithm is used for a quick preliminary search of the best local alignment region, whereas the SW algorithm does the actual alignment. In one embodiment, the default parameters of the SW algorithm are: match premium=+10; mismatch penalty=−20; and insertion/deletion penalty=−16.

For better results, in one embodiment, a vector part of the fragment should be masked before doing the alignment with consensus. A vector is a part of genome of the bacteria used as a host to multiply the DNA fragment before performing sequencing. After this multiplication, the DNA fragment is separated from the vector using a restriction enzyme. The restriction enzyme cleaves the DNA at specific sites called the restriction sites. The restriction sites are located on the vector, so some portion of the vector sequence still remains as a part of a fragment. To mask the vector part of the fragment, the fragment sequence is aligned against the known vector sequence.

In one embodiment, the results of alignment of the fragment sequence with the consensus sequence are then output into the training file in nine columns, one line per base. The first column may contain the position of the base in the fragment sequence. The second column may contain the fragment's base character at the position of the base in the fragment sequence such that '−' may be output in this column to represent a gap such as when consensus has a base at this position and the fragment does not. The third column may contain the position of the base in the consensus sequence. The fourth column may contain base character of the consensus at position of the base in the fragment sequence such that '−' may be output for the insertion when the fragment has a base at this position and the consensus does not. The fifth column may contain the number "1" if the base call is correct based the base character in the fragment matching the base character in the consensus, may contain the number "0" if the base call is incorrect, or may contain nothing, a blank space if there is no base call at the current position. The sixth, seventh, eighth and ninth columns contain the values of the trace parameters phr3, phr7, psr7 and pres, respectively, if the character in the second column does not represent a gap. If the character in the second column represents a gap, then the sixth, seventh, eighth and ninth columns all contain empty space.

As some of the bases may not represent the best alignment, they may be excluded from the training file. More specifically, if the fraction of errors within the best-alignment region exceeds 10%, the match between the fragment and consensus sequence may be regarded as occasional, and therefore, the whole alignment may be rejected and not stored in the training file. In addition, if two or more distinct regions in the consensus sequence are found which match the fragment within a specified threshold, namely, those with a fraction of errors≦85% within the best alignment region, then the consensus sequence may be regarded as having repeats, and all of the alignments may be rejected such that the sample file may be ignored.

2. Generating a Lookup Table a. Generating an Ordered List of Unique Values of Trace Parameters

The values of each trace parameter are read from the training file and are then sorted by value. If two or more identical values of the same trace parameter are found, they will be "merged" into a single "unique" value which will be assigned a weight equal to the number of identical values for which this parameter is found. At the conclusion of this procedure, four couples of arrays are created. Each couple consists of an ordered double type array of unique values $\{U_i\}$ of the trace parameter and integer array of their weights $\{w_i\}$, both the arrays having the same length K: $U_1$, $U_2$, $U_3$, . . . $U_K$ and $w_1$, $w_2$, $w_3$, . . . $w_K$.

b. Generating a List of Threshold Values

A list of trace parameter threshold values is generated by partitioning values of a given trace parameter into a number of groups, which are referred to as bins. Bins have the following characteristics: first, different bins contain approximately the same number of parameter values; and, second, bins are ordered such that each parameter value in a given bin is greater than any parameter value in the previous bin and less than any parameter value in the next bin. The thresholds are defined as the boundaries between neighboring bins. These two characteristics can only be satisfied if all the values of a given trace parameter are distinct. In this situation, the expected occupancy of a bin is equal to the ratio of the total number of good bases used for training to the desired number of thresholds, M, which is specified by a user of the training method. In one embodiment, it has been found beneficial to set M to equal 50. In practice, however, trace parameters computed for different bases may have identical values. As mentioned above, these values may be merged into unique values, and each unique value may be assigned a weight. If the weight of a given unique value exceeds the expected occupancy of a bin, then it should occupy a particular bin alone. In other words, a unique value can not be "split" between two or more bins, otherwise, the second characteristic will not be met.

In one embodiment, the thresholds of the trace parameters are computed. The trace parameters, represented by weighted unique numbers, are then partitioned into bins according to the following method. First, the expected occupancy of the first bin is computed as $S_1=N/M$, where S refers to occupancy, N is the total number of bases stored in the training file, and M is the specified number of bins or thresholds to be used. The value of the last threshold is equal to the largest unique value of trace parameter. Second the smallest unique value is assigned to the first bin. Third, the expected occupancy of the first bin is compared to the weight of the first unique value. That is, if $w_1>S_1$, then the next unique value will be assigned to the next bin, the value of the first threshold, $thr_1$, will be determined as $thr_1=(U_1+U_2)/2$, and the expected occupancy of the second bin will be determined as: $S_2=(N-w_1)/(M-1)$. However, if $w_1<S_1$, another comparison is made. If $w_1+w_2>S_1$, the two numbers, $w_1$ and $w_1+w_2$ are compared. If the first number $w_1$ is closer to the expected occupancy of the first bin, $S_1$, then the first bin is processed as described above. If the second number, the sum $w_1+w_2$, is closer, then both the first and second unique numbers are assigned to the first bin, the third unique number is assigned to the second bin. The first threshold is determined as $thr_1=(U_2+U_3)/2$, and the expected occupancy of the second bin is calculated as $S_2=(N-w_1-w_2)/(M-1)$. Otherwise, the list of unique numbers is scanned until a number $U_i$ is found such that $$w_1+w_2+\ldots+w_{i-1}<S_1$$

and $$w_1+w_2+\ldots+w_i>S_1.$$

Then, if $$|w_1+w_2+\ldots+w_{i-1}-S_1|<|w_1+w_2+\ldots+w_i-S_1|,$$

the first bin is populated with $w_1, w_2, \ldots w_{i-1}$ and set $$S_1=(N-w_1-w_2-\ldots-w_{i-1})/(M-1), \text{thr}_1=(U_{i-1}+U_i)/2.$$

Otherwise, the first bin is populated with $w_1, w_2, \ldots w_i$ and set $$S_1=(N-w_1-w_2-\ldots w_{i-1}-w_i)/(M-1), \text{thr}_1=(U_i+U_{i+1})/2.$$

Fourth, all subsequent bins are populated as described in the third step,

C. Generating the Table

After the bins are populated, lookup table entries are generated. First, a cut (i, j, k, l) is defined to be a rectangle in a four dimensional space of trace parameters, which includes all the bases with trace parameters in the range $phr3 \leq phr3\_thr_i$, $phr7 \leq phr7\_thr_j$, $psr7 \leq psr7\_thr_k$ and $pres \leq pres\_thr_l$, where i, j, k and l range between 1 and M, and M is the number of thresholds for each of four trace parameters. There are $M^4$ cuts in all. A list of all considered cuts is created.

Let $\text{err}_{i, j, k, l}$ and $\text{corr}_{i, j, k, l}$ be the total number of erroneous and correct base calls in the cut (i, j, k, l). Then, we define the error rate for the cut by:

$$e_{i,j,k,l} = \frac{\delta_{i,j,k,l} + err_{i,j,k,l}}{\delta_{i,j,k,l} + err_{i,j,k,l} + corr_{i,j,k,l}}.$$

The corresponding quality value is defined by:

$$QV_{i,j,k,l} = -10 \cdot \log_{10} e_{i,j,k,l}.$$

Here, $$\delta_{i,j,k,l} = \begin{cases} 0, & err_{i,j,kj,l} > 0; \\ 1, & err_{i,j,k,l} = 0. \end{cases}$$

is a small-sample correction that may be added to insure that both the numerator and denominator are positive even when $err_{i,j,k,l}=0$.

The following two steps are then iterated to create the lookup table. First, the cut (i, j, k, l) for which $QV_{i, j, k, l}$ is largest is found. If two or more cuts with the largest QV are found, the cut which contains the larger total number of bases, $err_{i, j, k, l}+corr_{i, j, k, l}$ is selected. If there is more than one of these, the cut for which the sum of the indexes, i+j+k+l, is highest is selected. The value $QV_{i, j, k, l}$ and threshold values $phr3\_thr_i$, $phr7\_thr_j$, $psr7\_thr_k$ and $pres\_thr_l$ are then output. The cut (i, j, k, l) is then deleted from the list of considered cuts. Second, for each remaining cut (i', j', k', l'), the counts $err_{i', j', k', l'}$ and $corr_{i', j', k', l'}$ are adjusted by deleting the bases which it shared with cut (i, j, k, l). The values $e_{i', j', k', l'}$ and $QV_{i', j', k', l'}$ are then recomputed using the new values. If $err_{i', j', k', l'}$ and $corr_{i', j', k', l'}$ are 0 for all remaining cuts, the generation ends. Otherwise, generation continues with the first step.

For a typical value of M=50, there are $M^4$=6.25 million cuts in all, so the procedure of adjusting the base counts in each cut after the cut (i, j, k, l) with largest $QV_{i, j, k, l}$ is found may be computationally slow. To accelerate this procedure, a 4-dimensional dynamic programming algorithm is implemented, whereby the base counts for the current cut are computed using the base counts of a few previous cuts in the list of all cuts. The number of correct base calls $corr_{i, j, k, l}$ and the number of erroneous base calls $err_{i, j, k, l}$ are determined for all values of i, j, k, and l as follows. Let c(i,j,k,l) be the number of correct base calls in the cut (i,j,k,l) and let b(i,j,k,l) be the number of correct base calls in the bin (i,j,k,l), where i, j, k and l range between 1 and M, and M is the number of thresholds for each of four trace parameters. To account for boundary conditions, let the value of c(i,j,k,l) be 0 if i=0 or j=0 or k=0 or l=0. The recursive relationship used by the dynamic programming algorithm is $$c(i,j,k,l)=b(i,j,k,l)+c(i-1,j,k,l)+c(i,j-1,k,l)-c(i-1,j-1,k,l)+c(i,j,k-1,l)-c(i-1,j,k-1,l)-c(i,j-1,k-1,l)+c(i-1,j-1,k-1,l)+c(i,j,k,l-1)-c(i-1,j,k,l-1)-c(i,j-1,k,l-1)+c(i-1,j-1,k,l-1)-c(i,j,k-1,l-1)+c(i-1,j,k-1,l-1)+c(i,j-1,k-1,l-1)-c(i-1,j-1,k-1,l-1).$$

The same recursive relationship applies when we alternatively let c(i,j,k,l) be the number of erroneous base calls in the cut (i,j,k,l) and let b(i,j,k,l) be the number of erroneous base calls in the bin (i,j,k,l), where i, j, k and l range between 1 and M.

The use of the dynamic programming algorithm for the rapid generation of a site specific lookup table is a significant improvement of the method described herein over prior art systems that maintain a fixed lookup table. This algorithm allows complete training of the system on a typical dataset comprised of a few thousands sample files in just a few hours. That means customized calibrations of the system on the data generated by any particular user at any particular site can be derived quickly and used instead of a single generic calibration (i.e., lookup table) provided by prior art systems such as Phred. Because the electropherograms produced by DNA sequencers on different sites generally differ in characteristic peak heights, shapes and/or spacing, the trace parameters computed from these data will also differ from one site to another. Thus, more reliable predictions of quality values for bases sequenced at a given site can be made if a lookup table generated from the data produced at the site is used.

What is claimed is:

1. A machine readable medium having stored thereon instructions which when executed by a processor cause a machine to perform operations comprising:
processing a plurality of information obtained from an electropherogram output by a base calling system;
creating a plurality of refined base calls using a plurality of original base calls and a plurality of intrinsic peak characteristics;
assigning a quality value to each of the plurality of refined base calls using the plurality of intrinsic peak characteristics; and
training by generating a training file and look-up table, wherein generating the training file comprises:
extracting and processing a group of electropherograms from at least one sample file;
determining called base sequences for each fragment in each electropherogram;
aligning the called base sequences with a corresponding consensus sequence to identify correct and erroneous base calls;
computing trace parameters for each base call of the called base sequences; and
writing the base calls as base call data and the trace parameters to the training file.

2. The machine readable medium of claim 1 wherein generating the look-up table comprises:
extracting the base call data and the trace parameters from the training file;
generating a set of trace parameter threshold values by partitioning the trace parameters into a plurality of bins;
populating the plurality of bins with the base calls;
defining a group of considered cuts; and
iteratively performing the following until a number of erroneous base calls for each cut of the group of considered cuts is zero;
computing quality values for each cut of the group of considered cuts;
selecting a largest quality value cut as the considered cut having the largest quality value of the group of considered cuts;
storing the largest quality value and corresponding threshold values in the look-up table;
deleting the largest quality value cut from the group of considered cuts; and
adjusting a base call count for the group of considered cuts by deleting those base call counts shared with the largest quality value cut.

3. The machine readable medium of claim 2 wherein adjusting the base call count comprises:
computing using a four dimensional dynamic programming algorithm the base call counts for a current cut using the base call counts of a system defined number of neighboring cuts and a current bin.

4. The machine readable medium of claim 1, wherein the operations further comprise:
determining a valve corresponding to a fraction of errors within the alignment of said base-called sequence and said consensus sequence;
determining if the value exceeds a predetermined threshold; and
removing the base calls and associated trace parameters from the training file if said value exceeds said predetermined threshold.

5. The machine readable medium of claim 4 wherein the predetermined threshold is approximately 10%.

6. The machine readable medium of claim 1, wherein the operations further comprise:
determining if two or more distinct regions in the consensus sequence have a fraction of errors below a specified threshold when aligned with the base-called sequence; and
deleting the sample file if at least two of said one or more distinct regions have a fraction of errors less than a specified threshold when aligned with the base-called sequence.

7. The machine readable medium of claim 6 wherein the specified threshold is approximately less than 85%.

8. A method for obtaining information from a base calling system, the method comprising:
processing a plurality of information obtained from an electropherogram output by the base calling system;
creating a plurality of refined base calls using a plurality of original base calls and a plurality of intrinsic peak characteristics; and
assigning a quality value to each of the plurality of refined base calls using the plurality of intrinsic peak characteristics.

9. The method of claim 8 wherein the processing comprises:
detecting a plurality of peaks;
expanding the plurality of peaks into a plurality of expanded peaks; and
resolving the plurality of expanded peaks to create a plurality of intrinsic peaks having the plurality of intrinsic peak characteristics.

10. The method of claim 9 wherein the detecting comprises:
identifying a plurality of inflection points; and
selecting the plurality of peaks based on the plurality of inflection points.

11. The method of claim 10 wherein the detecting further comprises:
computing a plurality of apparent peak characteristics.

12. The method of claim 10 wherein the selecting comprises:
ignoring those peaks that have an area under the peak that is smaller than an average per-peak area of a plurality of consecutive preceding peaks.

13. The method of claim 9 wherein the expanding comprises:
scanning to the left from a left inflection point of each peak of the plurality of peaks to determine an expanded left boundary for the peak; and
scanning to the right from a right inflection point of each peak of the plurality of peaks to determine an expanded right boundary for the peak.

14. The method of claim 13 wherein the scanning to the left comprises:
if a zero signal is detected, designating a location at which the zero signal is detected as the left expanded boundary for the peak;
if the beginning of a trace is detected, designating a location at which the beginning of a trace is detected as the left expanded boundary for the peak;
if a local minimum is detected, designating a location at which the local minimum is detected as the left expanded boundary for the peak;
if a right inflection point of a previous peak is detected, designating a location at which the right inflection point of the previous peak is detected as the left expanded boundary for the peak; and if the left expanded boundary is to the left of a right expanded boundary of the previous peak, redefining the left expanded boundary of the peak and right expanded boundary of the previous peak as a midpoint between a left inflection point of the peak and the right inflection point of the previous peak.

15. The method of claim 13 wherein the scanning to the right comprises:

if a zero signal is detected, designating a location at which the zero signal is detected as the right expanded boundary for the peak;

if the end of a trace is detected, designating a location at which the end of the trace is detected as the right expanded boundary for the peak;

if a local minimum is detected, designating a location at which the local minimum is detected as the right expanded boundary for the peak;

if a left inflection point of a next peak is detected, designating a location at which the left inflection point of the next peak is detected as the right expanded boundary for the peak;

if the right expanded boundary is to the right of a left expanded boundary of the next peak, redefining the right expanded boundary of the peak and left expanded boundary of the next peak as a midpoint between a right inflection point of the peak and the left inflection point of the next peak.

16. The method of claim 13 wherein the expanding further comprises:

classifying each of the expanded peaks as single or multiple based on the type of expanded left boundary and the type of expanded right boundary.

17. The method of claim 9 wherein the resolving comprises:

fitting the plurality of expanded peaks using a model of a peak shape; and computing a peak resolution.

18. The method of claim 17 wherein the fitting comprises:

deriving an equation representing an output of an electrophoresis of a plurality of DNA fragments, the equation accounting for electromigration and diffusion;

solving the equation to obtain a peak shape expression dependent on at least one of three adjustable parameters;

for each single peak of the plurality of expanded peaks, computing the plurality of intrinsic peak characteristics and the adjustable parameters using the peak shape expression and a set of single peak measurable characteristics; and for each multiple peak portion of the plurality of expanded peaks, inferring at least one intrinsic peak having the intrinsic peak characteristics.

19. The method of claim 18 wherein the inferring comprises:

computing a set of average measurable peak characteristics based on analysis of a set of preceding single peaks;

calculating a first invariant peak shape parameter and a second invariant peak shape parameter based on the set of average measurable peak characteristics; and for each of the intrinsic peaks, iteratively computing an intrinsic peak position and an intrinsic peak height based on the first invariant peak shape parameter, the second invariant peak shape parameter, the peak shape expression, and a set of intrinsic peak measurable characteristics.

20. The method of claim 17 wherein the computing a peak resolution comprises:

dividing an area under a curve representing the absolute value of the difference between an apparent peak signal of an apparent peak of the plurality of peaks and a corresponding fitted model peak by an area of the apparent peak.

21. The method of claim 8 wherein the creating comprises:

refining the plurality of original base calls using the plurality of intrinsic peak characteristics; and inserting a plurality of newly called bases using the plurality of intrinsic peak characteristics.

22. The method of claim 21 wherein the refining comprises:

calling true peaks;

resolving wide peaks;

re-calling unknown bases; and removing unmatched bases.

23. The method of claim 21 wherein the refining comprises:

for each known original base call, scanning a peak list of a particular color base;

if a peak is found at a location of the original base call and the peak is not assigned, calling the peak and assigning a corresponding base to the peak;

if the peak is found at the location of the original base call and the peak has been assigned, determining whether the peak is wide enough to be split;

if the peak is wide enough to be split, resolving the peak into two peaks, calling the two peaks, and reassigning the bases for the two peaks;

if the peak is not wide enough to be split or no peaks are found at the location of the original base, searching for an unassigned peak near the location of the original base call;

if the unassigned peak is found, calling the unassigned peak and assigning a base to the unassigned peak; and if no unassigned peak is found, temporarily designating the original base call as unknown.

24. The method of claim 21 wherein the refining comprises:

for each unknown base call, scanning four peak lists, one peak list for each base;

if at least one peak is found at a location of an unknown base call, obtaining a best peak;

if the best peak is not assigned, replacing the unknown base call with the corresponding base of the best peak, calling the best peak and assigning a corresponding base to the best peak;

if the best peak has been assigned, determining whether the best peak is wide enough to be split;

if the best peak is wide enough to be split, resolving the best peak into two peaks, replacing the unknown base with the corresponding best peak base, calling the two peaks, and assigning corresponding bases to the two peaks;

if the best peak is not wide enough to be split or no peaks are found at the location of the unknown base call, searching for a best unassigned peak near the location of the unknown base call;

if the best unassigned peak is found near the location of the unknown base call, replacing the unknown base with the corresponding best peak base, calling the peak and assigning the corresponding base to the peak; and if no best unassigned peak is found, rejecting the unknown base call.

25. The method of claim 21 wherein inserting the plurality of newly called bases comprises:

creating a multi-colored list of all peaks; and calling those peaks in the multi-colored list of all peaks that meet all of a plurality of criteria.

26. The method of claim 25 wherein the plurality of criteria comprise:

whether an index of an uncalled peak is greater than a specified minimum;

whether an intrinsic height of the uncalled peak is greater than an intrinsic signal of any other peaks at the position of the uncalled peak; and whether a spacing between two adjacent called peaks is large enough for insertion of a new base.

27. The method of claim 8 wherein assigning comprises:

computing a plurality of peak trace parameters for each intrinsic peak in the plurality of refined base calls; and obtaining a quality value for each base in the plurality of refined base calls from a look-up table.

28. The method of claim 27 wherein the plurality of peak trace parameter comprises:

a first peak height ratio for a current peak based on a first plurality of called peaks centered at a current peak;

a second peak height ratio for the current peak based on a second plurality of called peaks centered at the current peak;

a peak spacing ratio for the current peak based on a largest peak spacing and a smallest peak spacing of the second plurality of called peaks centered at the current peak and a peak resolution.

29. The method of claim 28 wherein the first plurality of called peaks centered at the current peak comprises three called peaks, and wherein the second plurality of called peaks centered at the current peak comprises seven called peaks.

30. The method of claim 27 wherein the obtaining comprises:

selecting the quality value from the look-up table from the row in the look-up table in which a plurality of table trace parameters in the row of the look-up table each exceed the plurality of peak trace parameters for a current peak.

31. The method of claim 8 further comprising:

training, wherein the training includes generating a training file and a look-up table.

32. The method of claim 31 wherein the training is conducted at each of a plurality of user locations based on a plurality of characteristics and a plurality of requirements of each of the plurality of user locations.

33. The method of claim 31 wherein generating the training file comprises:

extracting and processing a group of electropherograms from at least one sample file;

determining called base sequences for each fragment in each electropherogram;

aligning the called base sequences with a corresponding consensus sequence to identify correct and erroneous base calls;

computing trace parameters for each base call of the called base sequences; and writing the base calls as base call data and the trace parameters to the training file.

34. The method of claim 33 wherein generating the look-up table comprises:

extracting the base call data and the trace parameters from the training file;

generating a set of trace parameter threshold values by partitioning the trace parameters into a plurality of bins;

populating the bins with the base calls;

defining a group of considered cuts; and iteratively performing the following until a number of erroneous base calls for each cut of the group of considered cuts is zero;

computing quality values for each cut of the group of considered cuts;

selecting a largest quality value cut as the considered cut having the largest quality value of the group of considered cuts;

storing the largest quality value and corresponding threshold values in the look-up table;

deleting the largest quality value cut from the group of considered cuts; and adjusting a base call count for the group of considered cuts by deleting those base call counts stared with the largest quality value cut.

35. The method of claim 34 wherein the adjusting comprises:

computing using a four dimensional dynamic programming algorithm the base call counts for a current cut using the base call counts of system defined number of neighboring cuts and a current bin; and for each multiple peak portion of the plurality of peaks, breaking the multiple peak portion into at least two descendent peaks, and computing the plurality of intrinsic peak characteristics for each of the descendent peaks using the peak shape expression.

36. A machine readable medium having stored thereon instructions which, when executed by a processor, cause the machine to perform operations comprising:

processing information obtained by a base calling system from an electropherogram output;

creating a plurality of refined base calls using a plurality of original base calls and a plurality of intrinsic peak characteristics; and assigning a quality value to each of the plurality of refined base calls using the plurality of intrinsic peak characteristics.

37. The machine readable medium of claim 36 wherein the processing comprises:

detecting a plurality of peaks;

expanding the plurality of peaks into a plurality of expanded peaks; and resolving the plurality of expanded peaks to create a plurality of intrinsic peaks having the plurality of intrinsic peak characteristics.

38. The machine readable medium of claim 37 wherein the detecting comprises:

identifying a plurality of inflection points; and selecting the plurality of peaks based on the plurality of inflection points.

39. The machine readable medium of claim 38 wherein the detecting further comprises:

computing a plurality of apparent peak characteristics.

40. The machine readable medium of claim 37 wherein the expanding comprises:
scanning to the left from a left inflection point of each peak of the plurality of peaks to determine an expanded left boundary for the peak; and
scanning to the right from a right inflection point of each peak of the plurality of peaks to determine an expanded right boundary for the peak.

41. The machine readable medium of claim 37 wherein the resolving comprises:
fitting the plurality of expanded peaks using a model of a peak shape; and
computing a peak resolution.

42. The machine readable medium of claim 41 wherein the fitting comprises:
for each single peak of the plurality of expanded peaks, computing the plurality of intrinsic peak characteristics and the adjustable parameters using the peak shape expression and a set of single peak measurable characteristics; and
for each multiple peak portion of the plurality of expanded peaks, inferring at least one intrinsic peak having the intrinsic peak characteristics.

43. The machine readable medium of claim 42 wherein the inferring comprises:
computing a set of average measurable peak characteristics based on analysis of a set of preceding single peaks;
calculating a first invariant peak shape parameter and a second invariant peak shape parameter based on the set of average measurable peak characteristics; and
for each of the intrinsic peaks, iteratively computing an intrinsic peak position and an intrinsic peak height based on the first invariant peak shape parameter, the second invariant peak shape parameter, the peak shape expression, and a set of intrinsic peak measurable characteristics.

44. The machine readable medium of claim 41 wherein computing the peak resolution comprises:
dividing an area under a curve representing the absolute value of a difference between an apparent peak signal of an apparent peak of the plurality of peaks and a corresponding fitted model peak by an area of the apparent peak.

45. The machine readable medium of claim 36 wherein creating comprises:
refining the plurality of original base calls using the plurality of intrinsic peak characteristics; and
inserting a plurality of newly called bases using the plurality of intrinsic peak characteristics.

46. The machine readable medium of claim 45 wherein the refining comprises:
calling true peaks;
resolving wide peaks;
re-calling unknown bases; and
removing unmatched bases.

47. The machine readable medium of claim 45 wherein the refining comprises:
for each known original base call,
scanning a peak list of a particular color base;
if a peak is found at a location of the original base call and the peak is not assigned, calling the peak and assigning a corresponding base to the peak;
if the peak is found at the location of the original base call and the peak has been assigned, determining whether the peak is wide enough to be split;
if the peak is wide enough to be split, resolving the peak into two peaks, calling the two peaks, and reassigning the bases for the two peaks;
if the peak is not wide enough to be split or no peaks are found at the location of the original base, searching for an unassigned peak near the location of the original base call;
if the unassigned peak is found, calling the unassigned peak and assigning a base to the unassigned peak; and
if no unassigned peak is found, temporarily designating the original base call as unknown.

48. The machine readable medium of claim 45 wherein the refining comprises:
for teach unknown base call,
scanning four peak lists, one peak list for each base;
if at least one peak is found at a location of an unknown base call, obtaining a best peak;
if the best peak is not assigned, replacing the unknown base call with the corresponding base of the best peak, calling the best peak and assigning a corresponding base to the best peak;
if the best peak has been assigned, determining whether the best peak is wide enough to be split;
if the best peak is wide enough to be split, resolving the best peak into two peaks, replacing the unknown base with the corresponding best peak base, calling the two peaks, and assigning corresponding bases to the two peaks;
if the best peak is not wide enough to be split or no peaks are found at the location of the unknown base call, searching for a best unassigned peak near the location of the unknown base call;
if the best unassigned peak is found near the location of the unknown base call, replacing the unknown base with the corresponding best peak base, calling the peak and assigning the corresponding base to the peak; and
if no best unassigned peak is found, rejecting the unknown base call.

49. The machine readable medium of claim 45 wherein the inserting the plurality of newly called bases comprises:
creating a multi-colored list of all peaks; and
calling those peaks in the multi-colored list of all peaks that meet all of a plurality of criteria.

50. The machine readable medium of claim 49 wherein the plurality of criteria comprises:
whether an index of an uncalled peak is greater than a specified minimum;
whether an intrinsic height of the uncalled peak is greater than an intrinsic signal of any other peaks at the position of the uncalled peak; and
whether a spacing between two adjacent called peaks is large enough for insertion of a new base.

51. The machine readable medium of claim 36 wherein the assigning comprises:
computing a plurality of peak trace parameters for each intrinsic peak in the plurality of refined base calls; and
obtaining a quality value for each base in the plurality of refined base calls from a look-up table.

52. The machine readable medium of claim 51 wherein the plurality of peak trace parameters comprises:
a first peak height ratio for current peak based on a first plurality of called peaks centered at a current peak;
a second peak height ratio for the current peak based on a second plurality of called peaks centered at the current peak;

a peak spacing ratio for the current peak based on a largest peak spacing and a smallest peak spacing of the second plurality of called peaks centered at the current peak; and a peak resolution.

53. The machine readable medium of claim 51 wherein the obtaining comprises:

selecting the quality value from the look-up table from the row in the look-up table in which a plurality of table trace parameters in the row of the look-up table each exceed the plurality of peak trace parameters for a current peak.

54. The machine readable medium of claim 36 containing further instructions which when executed by a processor cause the machine to perform operations comprising:

training by generating a training file and a look-up table.

* * * * *